(12) United States Patent
Romano

(10) Patent No.: US 7,798,181 B2
(45) Date of Patent: *Sep. 21, 2010

(54) MATERIAL(S)/CONTENT(S) MANAGEMENT METHOD AND APPARATUS

(75) Inventor: Jack W. Romano, Kirkland, WA (US)

(73) Assignee: Medindica-Pak, Inc., Kirkland, WA (US)

( * ) Notice: Subject to any disclaimer, the term of this patent is extended or adjusted under 35 U.S.C. 154(b) by 867 days.

This patent is subject to a terminal disclaimer.

(21) Appl. No.: 11/638,867

(22) Filed: Dec. 14, 2006

(65) Prior Publication Data

US 2007/0107798 A1    May 17, 2007

Related U.S. Application Data

(63) Continuation of application No. 10/258,751, filed as application No. PCT/US01/40668 on May 2, 2001, now Pat. No. 7,185,681.

(60) Provisional application No. 60/201,451, filed on May 3, 2000.

(51) Int. Cl.
    *B65B 1/04* (2006.01)
(52) U.S. Cl. .................... 141/9; 141/114; 141/100

(58) Field of Classification Search .................. 141/9, 141/10, 18, 100, 102, 104, 113, 114, 234, 141/236, 237; 383/9, 10, 904, 906; 604/410, 604/415, 416; 220/502
See application file for complete search history.

(56) References Cited

U.S. PATENT DOCUMENTS 7,185,681 B2 *  3/2007  Romano ...................... 141/9

* cited by examiner

*Primary Examiner*—Steven O Douglas

(57) ABSTRACT

Volumetric enclosure(s) provide methods and/or apparatus for teaching, generating and deriving supply chain efficiency improvement. Prime Manifold Enclosure(s) methods and/or apparatus provide for deriving and generating efficiency by volumetric displacement and volumetric replacement of dissimilar material(s) and volumetric displacement and volumetric replacement of material having dissimilar origin. Prime Manifold Enclosure(s) interposed for cooperative coaptation and flow path communication/continuity between gradient matrix flow paths for volumetrically displacing and volumetrically replacing of dissimilar materials, and volumetrically displacing and volumetrically replacing materials of dissimilar origin. In process flow continuity embodying volumetric displacement and replacement of distinct materials of distinct origin interposing manifolds comprising materials having rigid, and/or, semi-rigid, and/or, semi-flexible, and/or flexible characteristics are disclosed for ingressing and egressing fluent materials along gradient flow matrix patterns.

52 Claims, 5 Drawing Sheets

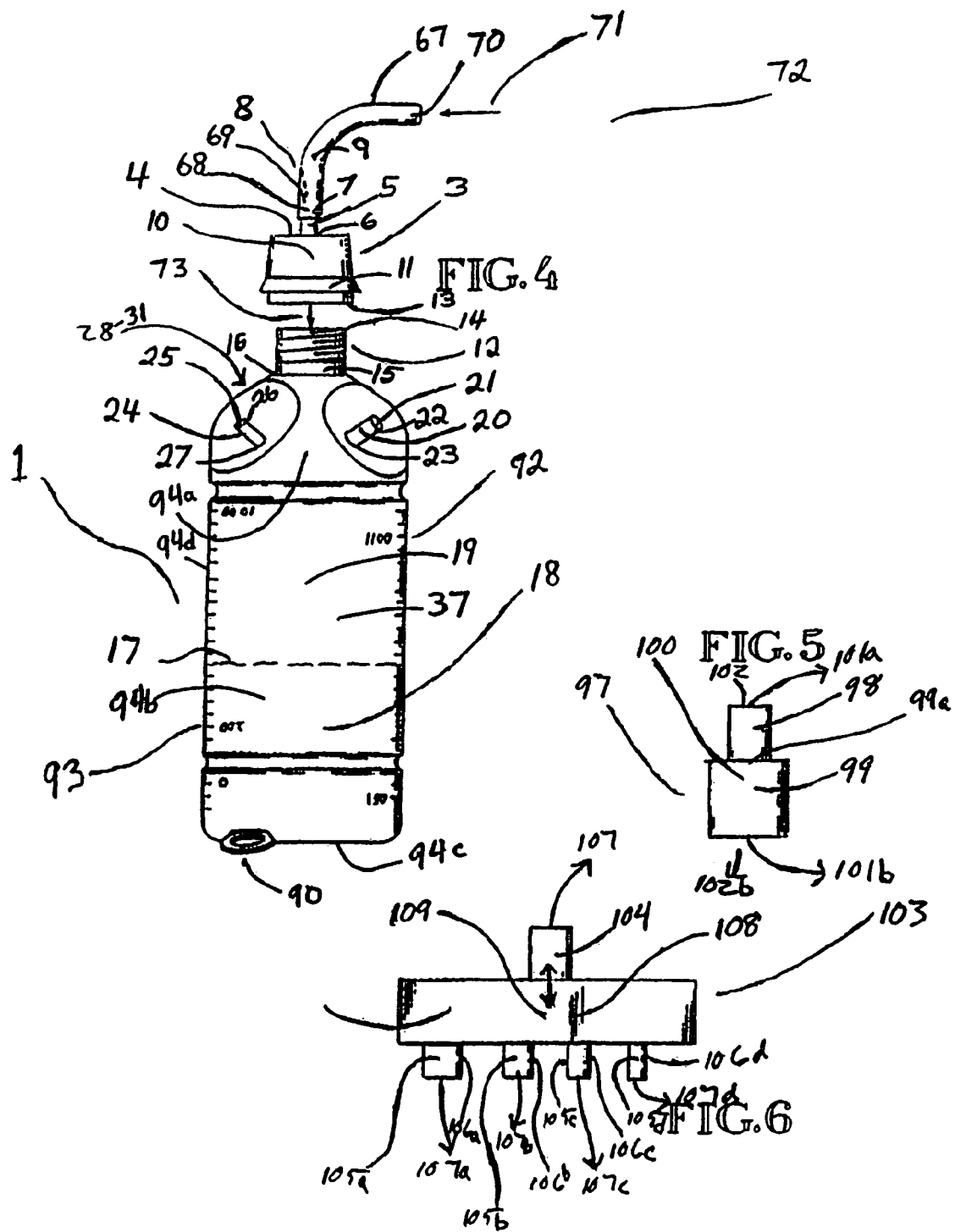

MATERIAL(S)/CONTENT(S) MANAGEMENT METHOD AND APPARATUS

This application is a continuation of U.S. patent application Ser. No. 10/258,751 which was filed in the United States on Oct. 28, 2002 now U.S. Pat. No. 7,185,681 which was based on PCT International Application No. PCT/US01/40668 filed on May 2, 2001 which claims the priority of U.S. Provisional Patent Application Ser. No. 60/201,451 which was filed on May 3, 2000.

BACKGROUND OF THE INVENTION

1) Field of the Invention

This invention relates to the field of handling of fluent materials and more particularly to enclosing material(s)/content(s) and containing/packaging, and the associated supply chain therefor.

2) Background of the Invention

Improving supply chain efficiency is of paramount importance in many industries. Such supply chain efficiency improvement would include the likes of cost reduction, waste reduction, inventory reduction, and products/supplies innovation which create procurement efficiency. The health care industry in particular has the highest initiatives for supply chain efficiency improvement. Cost control and cost reductions, reductions in medical waste, inventory management and other supply chain efficiency improvement's are of paramount concerns. The Efficient Consumer Health Care Response produced in 1996 bu CSC Consulting, Inc. as a text demonstrating the urgency for supply chain efficiency, and cost control in today's financially conscious health care community. Methods and/or Apparatus for deriving and generating efficiency improvements according the present invention are disclosed, and in part comprise volumetric displacement and volumetric replacement of dissimilar materials of dissimilar origins.

Health Care Materials Managers, purchasing personnel and providers have priority initiatives of realizing cost cutting, reducing medical waste, reducing inventory and standardizing supplies with the goal of overall cost savings across the board. The Congress of the United Sates of America has passed legislation such as the Balanced Budget Act, the Medical Waste Tracking Act, and other rules and regulations which place tremendous pressures on providers to implement cost efficiency improvements.

The supply chain comprise(s) in combination, many distinct manufacturing, product and health care practice modality disciplines. Naturally, each of these disciplines have evolved distinctly. Each discipline uses products combined with practice methods/techniques. Care modalities are derived from the combination. Intended indications are generally taught, disclosed and/or elucidated in the instructions for use, directions, and product literature which expresses in text, graphics and images die intended uses, indication(s) for, and how the product is intended to be used. These labels are typically required by regulatory governing bodies. These telltale labeling signs that accompany these products generally meet a regulatory clearance rating. At times, products are utilized off label. Each health care product is generally classified in some regulatory class or category.

Each distinct health care manufacturing/practice disciplines has evolved within respective discipline boundaries. Commodity types of products are generally deemed matured. Matured products usually have little efficiency improvement potential moving forward.

"Point of Consumption", for a particular product(s), manufacturing and practice captures the usage boundaries, and borders for which a particular innovation/invention has been created/anticipated.

The present invention, discloses methods and apparatus where invention/innovation traverses borders and boundaries, crossing and integrating "Points of Consumption" where need for efficiency improvement has been long felt and long overdue. The instant case defines efficiency improvements in ways not yet defined by the prior art.

The present invention teaches methods for deriving/generating universal containment applicability and provides apparatus for cooperative coaptation traversing distinct disciplines of the prior art. Heretofore, the inventor knows of no prior art, which anticipates the utility of the present invention. The present invention provides methods and apparatus having co-operative and co-coaptive prime manifold enclosures/fluent materials manifold(s) to derive/generate/create any multitude of desired flow pathway matrix for the purposes of supply chain efficiency improvements.

The prior art confers little in the way of efficiency improvement. Strictly speaking, the prior art is not systemized and/or structurally capable/compatible to provide the utility as disclosed with the present invention. The prior art anticipates and teaches inter-incompatibility, incapable of cooperation, and teaches toward structural incompatibility. The prior art teaches and anticipates separate and distinct disciplines having borders/boundaries without traverse, which maintains high cost of operations.

The present invention confers supply chain efficiency improvements, cost reduction, waste reduction, inventory reduction and labor savings reduction potential. The present invention discloses universal prime manifold enclosure apparatus that cooperatively traverses disciplines of the prior art allowing creative options for potential unprecedented supply chain savings. The present invention teaches and discloses methods for deriving supply chain efficiency solutions specifically selectable for generation of any combination of efficiency measures as described herein. The present invention allows for various fluent flow matrix/patterns derivable from and allowing the impelling of fluent materials traversing disciplines as provided by the methods and apparatus disclosed herein. Coaptation means, associated with each prime materials manifold allows for impelling fluent materials at choice through traditional "Point of Consumption" boundaries, divisions of separateness and distinction via common cooperative connectable fitting.

The present invention discloses and teaches a system which will empower the provider for the first time with the option to evaluate and balance incoming fluent materials(s) and outgoing fluent material(s) traversing disciplines with a coordinated, and cooperative composite impelling matrix flow pathway(s). The present invention operates to defines new points of consumption.

The prior art teaches towards segmentation, separation, differentiation and distinction between disciplines in manufacturing, functional dynamics, treatment/care practice modalities, assessment and planning resulting in higher costs, higher amount of medical wastes, higher inventory carrying costs, and lower supply chain efficiency associated therewith among other things.

The present invention teaches away from the prior art. The present invention teaches the coordination, and cooperative integration and fluent flow matrix pathway blending, traversing traditionally distinct disciplines of manufacturing, functional dynamics, treatment/care practice modalities among other things.

DESCRIPTION OF PRIOR ART

In order to get a better understanding of the present prime manifold enclosure(s) invention, it will be helpful to describe the prior art and the problems with the prior art. The prior art consists of a variety of containers and containment methods and apparatus for the handling of fluent materials. These containers are used for many purposes. The prior art products comprise traditional containers used for the packaging of the following types of products among combinations and sub-combination thereof. a) Water for Injection (WFI) based products. b) Pour bottles of various sizes and shapes. c) large volume parenteral solutions. d) small volume parenteral solutions. E) water for injection based combination products. F) Sterile water, g) sterile saline in various concentrations. H) lactated ringers. I) dextrose. J) irrigating solutions K) other intravenous solution bags/containers. The prior art is available traditionally in rigid, semi-rigid, semi-flexible and flexible materials/varieties. These products have been anticipated to contain materials/products in specific ways. Most all of these products have inner containment space which, but unlike the present invention, are missing the structural cooperative coaptation compatibility to provide supply chain efficiency improvement(s) that are provided by the methods and apparatus of the present invention. As a result these prior art containers bring the many problems as defined herein which fall short in delivery of the much needed supply chain efficiency improvements demanded by the financial strains in the current health care environment. One such prior art patent is U.S. Pat. No. 4,803,102 to Raniere et al. This describes the typical flexible type of traditional container methods and apparatus for the containment of intravenous fluids. This patent is directed at laminating flexible sheets, teaches processes for manufacturing the container within the discipline and does not anticipate or define the teachings and disclosures of the instant case. Another prior art patent, U.S. Pat. No. 5,971,965 issued to Mayer discloses needle-less access to a container typically used for the containment of intravenous fluids. This patent does not address supply chain efficiency, traversing across dynamic disciplines for environmental reasons etc. Another prior art patent is U.S. Pat. No. 3,915,212 issued to Bujan which discloses novel ways to conveniently mix substances within a container traditionally. This patent also does not disclose, teach or anticipate the traversing, integrating and cooperation between disciplines to achieve supply chain efficiency. Another such prior art patent, U.S. Pat. No. 4,298,045 issued to Weiler et al disclosed a typical traditional pour bottle. This patent discloses incremental structural improvements in a mature product industry. This prior art patent neither anticipates, teaches or discloses the novel methods and apparatus disclosed by the present fluent materials manifold invention. Each of these types of traditional prior art containers is available in many sizes and have numerous structurally peripheral differences each of which do not anticipate the importance of supply chain efficiency improvements. None of the prior art teaches traversing dynamic disciplines, utilization of a unitary fluent materials manifold for traversing distinct disciplines. None of the prior art reaches supply chain efficiency by cooperative coaptation between disciplines. None of these prior art patents teaches integration, coordination and amalgamation of disciplines by the interposing of a fluent materials manifold among and between these disciplines for the purposes of supply chain efficiency improvements. Again, each of these prior art patents teaches towards incremental improvements/innovation to anticipating inter disciplinary advancement, without traverse.

Additional products of the prior art involve additional types of containers, bags, and containment methods and apparatus teaching compatibility that is inter-disciplinary, without traverse. These prior art containers include, infusion reservoirs, wound drain reservoirs, suction and collection canisters, urinary/bladder drainage bags, bulb syringes, graduated pitchers for saline and other irrigation solutions, sterile processing of saline pitchers. There are many problems with these prior art patents. Many of these products have evolved to a commodity status and are defined by being entrenched, each within its own classification of discipline of manufacturing, product apparatus, indications for use, structure, specific discipline practice modality. It is the view of the inventor that none of these products satisfy the health care financial changes of the times. The Balanced Budget Act and the Medical Waste Tracking Act are examples of the tremendous pressure for which providers are bound to realize supply chain efficiency. These products must undergo sufficient and significant change to realize cost reduction, inventory reduction, inventory management reduction, reduction in medical waste and garner environmental improvements/advantages.

The question then becomes, how does one go about satisfying the need for supply chain efficiency improvement. The inventor uses analysis of process economics. The term process economics is a term of the inventors mind, and is defined as the analysis and study of problems between processes and structures that interfere with improvement. Process economics in this instance has evolved to provide the methods and apparatus of the present invention, which to the inventors mind defines new standards of efficiency.

Problems with Prior Art

One problem with the prior art is that there are no teachings or instructions for use, or sales marketing or literature elucidating any telltale signs of how to go about supply chain efficiency improvements. Another problem with the prior art is that there is no structural cooperative coaptation for in process continuity and flow pathway matrix integration.

Still another problem with the prior art is structural in that each of these containers are mismatched structurally and are not compatible, or capable of structural coaptation. Still another problem with the prior art is the inter-incompatibility for mutually sizing, fitting shaping and matching together for cross discipline composite flow path matrix amalgamation/unification.

The prior art also does not teach streamlining distribution, or reducing inventory. It does not teach matching incoming and outgoing materials volumes along a common fluent flow path matrix.

The prior art cannot help the provider select options having more efficiency outcomes. Still another problem with the prior art is that these particular container(s)/containment methods are not anticipated for or cooperative with structural coaptation to traverse across a variety of distinct disciplines for forming flow matrix pathway patterns which confer efficiency advantages.

Another problem with the prior art is the anticipation by structure, apparatus, methods and labeling that the traditional disciplines are non traversable across points of consumption, treatment modalities, practice modalities, technical sequences, modes of care, methods of treatments, manufacturing disciplines, market segments, product categories, regulatory classifications, traditional boundaries, commodity product borders, distribution patterns, supply chain organization methods, supply ordering indices, inventory carrying methods, and the like each separately and cooperatively anticipated.

Another problem with the prior art is that there is no teaching, or anticipation of cooperative coaptation or forming flow matrix patterns traversing: distinct dynamic disciplines, importation and deportation of materials, dispensers and receptacles, dispensing and collecting, delivery and disposal, administering and dumping, between incoming and outgoing materials, volumetric planning and volumetric wasting, counterbalancing of administering patient fluid volumes and the counterbalancing of outgoing patient fluid volumes, ingressing and the egressing, egressing and the ingressing, impelling and the expelling, expelling and the impelling, filling and emptying, manufacturing and treatment, treatment and dynamic function, between dynamic function and manufacturing, assimilation and excretion, absorption and secretion.

Another problem with the prior art is that the prior art does not provide for cooperative coupling traversing distinct disciplines of care such as irrigating, suctioning, flushing in, pulse lavage, fluid volume administration and managing, soaking and cleaning, collection, dumping, washing.

Another problem with the prior art is that it does not provide for coaptation methodologies involving the coordination and adaptation linking impelling, ingressing, egressing, volumetric assessment and in-going and outgoing consumption between separate points of consumption.

Another problem with the prior art is the prior art does not provide systemized and convertible integration regarding impeller source dynamics with respect to self impelling, alternative impelling, positional impelling, orientational impelling, memory recall impelling co-impelling and impelling from within.

Another problem with the prior art is the lack of "in process continuity" associated with the non-traversing distinct dynamic disciplines.

Reasons for Prior Art Problems

These problems are evident in the history and evolution of each of the distinct disciplines of the each or the prior art fields. The prior art has been largely status quo, in context with supply chain efficiency and does not anticipate the present invention for many reasons. One reason is that the intention of the present invention is to cross the borders and boundaries tenet to the prior art defining dynamically different and distinct characteristics.

Therefore there is a lack of conceptual continuity flowing across these borders and boundaries, non-traversable disciplines of the prior art. The teaching and disclosures of the instant invention result from a unique, rare and unusual exposure of the inventor, which exposure traverses across each of the disciplines discussed herein. There are a number of specific examples and some of these examples surround the medical field and some of these examples are defined by the evolution of the commodity markets outside of the medical field. The prior art defines product markets which have become mature. Markets that are deemed mature often, and generally have reached a state of maximum efficiency thus rendering them commodity status.

Certain structural tenets in combination with a number of separate static institutions surrounding the field of this invention raise barriers to creativity, and make invention especially difficult. These regimented institutions include regulatory classification, regulatory indices, corporate and brand name identity, regulatory registration processes and approvals, product sedimentation, product segmentation, product differentiation, product focus, separate healthcare treatment modalities, separate policies, separate procedures, distinct standards of practice. Each separate and distinct discipline with unassociated dynamics makes it extremely difficult to freely conceptually traverse these distinct dynamics.

Objects/Purpose of the Invention

One object of the invention is to provide methods and/or apparatus for volumetric displacement and volumetric replacement of dissimilar materials and to provide volumetric displacement and volumetric replacement of materials of dissimilar origin.

One object of the invention is to provide methods and/or apparatus having teachings, instructions, and telltale signs expressing in text, graphics and images, in any language for deriving supply chain efficiency as taught by the present invention.

Another object is to provide methods and/or apparatus having structural cooperative coaptation for in-process continuity and flow pathway matrix integrating multiple flow dynamics.

Still another object is to provide methods and/or apparatus for structural matching, and fitting for prime manifold enclosures to derive multiple in process integration of flow matrix pathways for a plurality of fluent flow dynamics.

Yet another object is to provide methods and apparatus for interposing fluent materials manifolds between flow path matrix passageway communication means/sites to traverse flow disciplines for flow pattern matrices amalgamation, continuity and unity.

Still a further object is to provide apparatus and methods to derive/generate supply chain efficiency improvements such as systems for cost reduction, inventory reduction, waste reduction and the like.

Another object of the invention is to provide methods and apparatus for counterbalancing incoming fluent material flow volumes with outgoing fluent materials flow volumes teaching deriving and generating options/choices to integrate and cooperate prime manifold enclosures for traversal across flow disciplines and flow pattern dynamics via novel flow matrix patterns.

Still a further object is to provide methods and apparatus teaching alternative flow pattern traversal options for operational efficiency in selection/procurement of supply sets/packs, by conferring supply chain improvement advantages by interposing cooperative prime manifold enclosures between distinct flow disciplines and patterns of fluent flow dynamics.

Another object of the invention is to provide methods and apparatus for procurement efficiency by allowing cooperative coaptation conferring supply chain efficiency improvement potential interposing prime manifold enclosure(s) traversal across matrices of fluent flow pathways and/or dynamic flow patterns.

Still a further object of the invention is to provide methods and/or apparatus for deriving efficiency options and choices by volumetric displacement and volumetric replacement of dissimilar materials, and/or volumetric displacement and volumetric replacement of materials of dissimilar origin for in process flow matrix continuity traversing across distinctions of fluent flow dynamics and/or flow matrix disciplines including, but not limited to: 1) points of consumption, 2) treatment modalities, 3) practice modalities, 4) technical sequences, 5) modes of care, 6) methods of treatment, 7) manufacturing disciplines, 8) methods of distribution arrangement, 9) market segments, 10) product classifications, 11) product categories, 12) product classes, 13) regulatory classifications, 14) regulatory categories, 15) traditional borders of distinction, 16) indications for use, 17) distribution patterns, 18) inventory carrying methods, 19) inventory space availability, 20) supply chain organization methods, 21) ordering indices, and the like, each separately, and/or collectively, for the purposes of supply chain efficiency improvement. It is understood that the 21 examples listed here are for illustration of some of the many embodiments which may be implemented under the scope of the appending claims and this list is not intended in any way to limit the scope of the claims.

Yet a further object of the invention is to provide methods and/or apparatus for volumetric displacement and volumetric replacement of dissimilar materials, and/or volumetric displacement and volumetric replacement of materials of dissimilar origin, traversing distinct fluent flow dynamics and/or flow matrix pattern disciplines interposing a prime manifold enclosure/fluent materials manifold between, but not limited to: 1) importation and deportation, 2) dispensers and receptacles, 3) dispensing and collecting, 4) delivery and disposal, 5) incoming and outgoing, 6) fluent material volume procurement and fluent materials volume wasting, 7) counterbalancing and administering incoming patient fluid volumes and counterbalancing and administering of outgoing patient fluid volumes, 8) impelling and expelling via ingressing, 9) impelling and expelling via egressing, 10) ingressing and egressing via impelling, 11) egressing and ingressing via expelling, 12) impelling and expelling, 13) expelling and impelling, 14) filling and emptying, 15) manufacturing and treatment, 16) treatment and dynamic function, 17) dynamic function and manufacturing, 18) assimilation and excretion, 19) absorption and secretion, 20) irrigation and collection, 21) collection and administration, 22) soaking and collection, 23) cleaning and collection, 24) soaking and excretion, 25) washing and voiding, 26) administration and voiding, 27) suctioning and administration, 28) irrigation and drainage, 29) administration and drainage, 30) irrigation and collection, 31) volume displacement and volume replacement, 32) pressure gradient implosion and pressure gradient explosion and the like, each separately or collectively practiced by the interposition of a prime manifold enclosure interposing a fluent flow matrix pathway therebetween. It is understood that the 30 examples listed here are for illustration purposes to show some of the many embodiments of the inventions and this list is not intended to limit the scope of the appending claims.

It is understood the object(s) of the invention is to provide methods and/or apparatus for volumetric displacement and volumetric replacement of dissimilar materials and volumetric displacement and volumetric replacement of materials of dissimilar origin, and that the fundamental purposes/objects disclosed in the instant case co-apply and extend to all of the stated listed objects/purposes distinctly and collectively.

One additional object of the invention is to provide methods and apparatus comprising cooperative coaptation among fluent materials manifold embodiments comprising: 1) flexible, 2) semi-flexible, 3) semi-rigid, and/or 4) rigid, materials.

Another object of the invention is to provide methods and apparatus for a prime manifold enclosure embodiments comprising; 1) flexible, 2) semi-flexible, 3) semi-rigid, and 4) rigid, materials.

Still a further object of the invention is to provide methods and apparatus for garnering efficiency improvements involving coaptation and cooperation among and between distinct disciplines of; 1) manufacturing, 2) labeling, 3) instructing, 4) practice modalities, 5) care/treatment, 6) product composites 7) component parts, 8) steps of practice, 9) product arranging and 10) procuring supplies into efficient sets.

Still a further object of the invention is to provide methods and apparatus for a prime manifold enclosure traversing cooperative coaptation between disciplines, points of consumption, treatment modalities, practice modalities, technical sequences, manufacturing disciplines, market segments, product categories, regulatory classifications, traditional borders, commodity markets/products, boundaries, distribution channels/pattern, supply chain organization, supply procurement procedures, inventory management, the traversal being any combination or sub-combination of the imposing of a prime materials manifold therebetween.

Still a further object of the invention is to provide methods and apparatus of the fluent materials manifold system embodying cooperative coaptation traversal between the disciplines of dispenser and receptacle, delivery and disposal, administration and dumping, incoming fluent.

Still a further object of the invention is to provide coordinated cooperative adaptation with a prime manifold enclosure traversing the supply chain disciplines of irrigating, suctioning, flushing, pulse ravaging, lavaging, administering soaking, cleaning, collection, dumping: arranging and selection of in-process continuity cooperatively and structurally traversing disciplines imposing a fluent materials manifold among and between impelling links, expelling links, egressing and ingressing links, fluid management, volumetric patient fluid volume assessment and management, hot and cold therapy treatments, self impelling, alternative impelling, positional impelling, orientational impelling, memory recall impelling and co-impelling.

Some material(s)/content(s) are required to meet certain sterility assurance level requirement (SAL) in the medical field. The container(s)/package(s) invention described herein provides methods and apparatus having structures that link manufacturing, plural purposes, through disposal, and provides coordinated structures, fittings, caps and closures so that the involved material(s)/content(s) is intended for and/or used in interconnection(s)/association(s) with, not only the "Initial/traditional purpose/indication(s)" filling, transport, storage, dispensing, pouring, using, releasing of sterile/other fluids, material(s)/content(s) and the like under various circumstances for various purposes, the present invention has means and/or uses for being fitted and/or used in association with and for carrying out the additional delivering and receiving, and the receiving and delivering of, and/or the ingress and egress, the egress and ingress of material(s)/contents(s), by a variety of ways, for a variety of functions and for a plurality of purpose(s)/indication(s) in new and novel coordinated manner(s)/system(s) which may have a positive impact on the supply chain. Such variety of uses of the present invention include, but are not limited to providing methods and apparatus involving newly arranged and coordinated connectability, inter-connectability, re-connectability and co-connectivity of and between communication passageways, and among and between material(s)/content(s) enclosures, which allows material(s)/content(s) to be co-mingled/managed between events/indications that occur along a supply chain, creating new and novel continuum of use/indication from manufacturing through disposal, and are not limited to use by/with connection(s), interconnection(s), re-connection(s), inter-communication(s), etc., along passageway(s), in connective combination(s), and/or by single communication pathway means as material(s)/contents(s) moves, to and from, from and to an event(s)/instance(s) of use to and from and from and to an enclosure/package. Material(s)/content(s) may move along passageway(s) by the externally applied forces urging and creating pressure(s), or by gravity, by vacuum, by suction, by association/re-association, self activated vacuum caused by shape memory or by mechanical or other combination's of remote and/or artificial means enacting upon and impacting a systems function, anywhere within/along the material(s)/content(s) passageway(s) enclosure(s) combination and in any manner which acts to allow movement/transport of material(s)/content(s) throughout a system and for a particular purpose. The invention also provides methods and apparatus having particular utility in the reduction and/or the elimination of the use of other plural (up to duplicate, triplicate, and quadruplicate, or more) container(s)/receptacle(s)/enclosure(s), allowing reduction of the numbers of containers/receptacles/enclosures employed for daily courses of care, operations, and impacting the associated supply chain that relate(s) thereto.

The prior art management of material(s)/content(s) has typically and traditionally been carried out using a variety of container(s)/package(s) made, labeled, packaged and used traditionally for an intended indication or purpose. Some of these prior art container/packages/enclosures are manufactured, labeled, packaged, distributed and used, relying on processes well know in the medical industry. Some of these well known processes include 1) blow, fill seal technology, 2) form fill seal technology, 3) processes used for intravenous solution(s) and intravenous bag manufacturing, large volume parenteral solutions and small volume parenteral solutions and related machinery and equipment, 4) Tubing extrusion, 5) standard molding and machining of connectors and fittings 6) caps and closures manufacturing and machine forming processes 7) integrated sterilization processes and methods among other well known processes used for manufacturing of and in conjunction with labeling equipment which is common to production of products that meet certain regulatory labeling sterility assurance level (SAL) requirements. These listed processes are well known to the industry and known to those skilled in these art fields.

Historically, the prior art has been anticipated for use with design outputs that meet design inputs in accordance with the prior art labeling and instructions for use.

Traditional prior art Sterile Water containers/packages receive, deploy and dispense material(s)/content(s) in ways based on traditional prior art labeled/indicated initial purpose fittings/configtirations-caps/closures, and then loose value because they are fitted/indicated with/for means to carry out the traditionally labeled/initially intended purpose. Prior art procedure irrigation fluids, and fluids for Arthroscopic irrigation. Urology irrigation and other material(s)/content(s) of body cavity/space (joint or other) infusion container/packages are contained within, deployed and dispensed based on traditionally labeled/indicated purpose prior art fittings/configurations in the traditional manner for initial purposes and the package/container looses value because they are fitted/indicated with/for means to carry out the traditionally labeled/indicated intended purpose. Traditional prior art collection enclosures, for the collection of blood, urine, wound drainage, ABCs and infections, plural cavities, cerebral spinal fluids the collection of the by products resulting from treatment have traditionally been fitted/used/indicated in traditional ways by the prior art, and not systemized or integrated to reduce regulated medical waste or reduce supply chain costs. Traditional prior art container/packaging has historically and commonly been made available in rigid, semi-rigid, and flexible embodiments. The prior art neither teaches or fairly suggests the utility, use, usefulness and the value as taught by the innovation disclosed by the present invention. Other uses such as blood bags, and the reprocessing of blood, such as re-infusion, and other such events may benefit from the methods and apparatus as disclosed by the present invention.

The utility of the present invention is not thought of without the intended application of re-processing and recycling. It is the view of the inventor, that with proper application and utilization, the utility of the present invention would confer greater efficiency improvements as disclosed/taught herein, whereas reprocessing delivers additional costs. Proper utilization of the present invention balances procurement, utilization and disposal to the maximum level of supply chain improvement efficiency.

The utility/indication of the present invention provides methods and apparatus for coordinating connectivity of enclosure(s), to and with a system(s) of passageway communication creating a new and novel linkage between material(s)/content(s) management enclosures and passageway connection means, linking the manufacturing, distribution, application and disposal of material(s)/content(s). The utility/indication of the present invention provides methods and apparatus for indicating and carrying out objects of the invention such as yielding manufacturing cost reductions, shipping/distribution cost reductions, inventory/cost reductions, handling cost reductions, medical waste cost, reduction and other reductions along the supply chain including activity based cost reductions. Due to the creation and application of this unique and novel system, the use/purchase of duplicate, triplicate, and in some instances quadruplicate (or more) container(s)/packages(s)-products along a chain/cycle of patient(s) treatment and care may be reduced. It is understood that the scope of the appended claims is intended to include any and all reprocessing and/or re-use of the present invention. It is understood that the treatment cycle may be profilactic, in advance of institutional care, in conjunction with institutional care, throughout care and through the rehabilitation and recover processes that result from the cycle of treatment. Treatment may be short term-short stay, intermittent, or long term or convalescent. Treatment is also not intended to be limited to care given by a provider. Treatment may be delivered or given by ones self, a family member or provided to an animal in any circumstances. Today's health care environment is driven by cost containment measures, and other measures which call for the reduction of costs, reduction of waste and a reduction in supply chain and activity based costs. Some applications of the invention disclosed herein may be utilized to reduce the number of prior art container(s)/package(s) by one. Some applications of the invention disclosed herein may be utilized to reduce the number of traditional prior art container(s)/package(s) by two. Some applications of the invention disclosed herein may be utilized to reduce the number of traditional prior art container(s)/package(s) by three. Some applications of the invention may be utilized to reduce the number of traditional prior art container(s)/package(s) by more than three. Such reduction's eliminates costs, and the need for purchase, delivery, storage, handling, inventory and use of certain other specialty types of container(s)/package(s). Such reductions also impact positively, the supply chain from raw materials to disposal, with regards to the utility of the present invention/system. Some applications of the invention allow for new uses, which may result in new and useful functional products/applications, where the invention stands in to perform as additionally indicated purpose(s)/function(s) in place of the traditionally indicated prior art ways. The present invention is intended to connect/communicate, fit/co-operate material(s)/content(s) container(s)/packages(s) with passageway communicating methods and apparatus so that the container(s)/package(s) may easily be systemized, adapted, coordinated and integrated for a variety of functions and a plurality of indication(s)/purposes along a cycle(s)/chain(s) of treatment(s)/care(s) uses involving various material(s)/content(s). The present invention thus applies and/or integrates a container/enclosure for cooperation among, between and with new and different points of consumption, uses, indication(s) and applications beyond the scope of the prior art indications for use. The integrated container(s)/package(s) invention as disclosed by the present invention and may be made from a variety of materials commonly used for such purposes, and the utility of the invention may be practiced and carried out in rigid, semi-rigid, semi-flexible and flexible types of container(s)/package(s). The invention may also be practiced in a form manufactured from polymer, plastic, metal, or paper fiber (wood pulp) based, or other materials or combinations thereof. The invention may also be practiced using many well know manufacturing processes, which include blow fill sea, form fill seal, composite plastic joining of films and sheets to form enclosures as commonly done with in the intravenous fluid industry, forming and joining of aluminum foils and other metal based films and sheets to form enclosures which may be used to enclosure material(s)/content(s) each of these manufacturing methods integrated with other cap and closure methods and apparatus in order to carry out the present invention.

The inventor is also not aware of any prior art which teaches the present invention, and how the present invention carries out the integration of manufacturing process through treatment modality and disposal as taught herein, for the purposes of reducing activity based costs, reducing medical waste, collecting material(s)/content(s), delivering material(s)/content(s), monitoring/balancing patient fluid volume levels. The present invention teaches towards integration, coordination, and reduction of container(s)/package(s), linking manufacturing, distribution through use, treatment indication, coordination collection and disposal, that result in lowering health care costs, reducing inventory expense, reducing product costs, reducing handing costs and lowering supply chain costs and providing multiple functions and purposes for a fundamental enclosure, among other things. It is understood for the purposes of this application, that the claims of lowering supply chain costs is not intended to relate to any particular pricing scheme found in the marketplace(s) practiced, however the supply chain costs savings potential is intended by the reduction in products and processes potentially eliminated account for the claims of positive impact on the supply chain.

BRIEF DESCRIPTION OF THE DRAWINGS

Each of the referenced pages of drawings show the primary object of the invention interposed between variable dynamic pressure gradients for the purposes of volumetric displacement and volumetric replacement of dissimilar materials and volumetric displacement and volumetric replacement of materials of dissimilar origin.

Each of FIGS. 1-7 define material(s)/content(s) enclosure/barrier structures whereby the enclosure/harrier is interposed between the material(s)/content(s) and its surroundings for the purposes of reciprocally keeping the material(s)/content(s) separate from the surrounding(s) area(s) and vice versa for delivery to and delivery from an instance of use along a flow matrix. Each of the herein referenced embodiments have/provide for unitary variable cubic capacity and are cooperatively coordinated and integrated for coaptation by maximum sizing, fitting application, matching and utility as disclosed herein. The prime manifold enclosure 1 of FIGS. 1-7 may be defined throughout as "prime manifold enclosure(s)" and/or "fluent materials manifold(s)". Each of the figures referenced herein show the "prime manifold enclosure(s)" interposed between system(s) of dynamic flow gradient matrices. Each of the figures referenced herein also shows the prime manifold enclosure(s) undergoing variant causes of pressure gradient changes. Each of the figures referenced herein show the prime manifold enclosure(s) pressure gradient changes caused from any number of origins along the flow matrix patil(s). The figures referenced herein show enclosure volume displacement and/or replacement as dynamic events along flow matrix pathways cause gradient pressure changes.

FIGS. 1-7 define embodiments of the invention being carried out with enclosure/barrier structure of the prime manifold enclosure/fluent materials manifold as will be described hereinafter as being made from either rigid material, semi-rigid/semi-flexible or flexible material. Each of the embodiments of FIGS. 1-7 are depicted as having/providing unitary variable cubic capacity.

FIG. 1 is a top front perspective view of an embodiment showing the prime manifold enclosure/fluent materials manifold material(s)/content(s) management invention enclosure/barrier filled with a solution (material(s)/content(s)) suitably prepared for sterile/medical procedures;

FIG. 2 is a bottom front perspective view of the prime manifold embodiment as hung in an inverted fashion, the access fitting on the cap/closure having been accessed by a passageway tubing/conduit connector at a passageway communication/connection site, for communication of the material(s)/content(s) with the course of treatment/care;

FIG. 2A is a tilted front elevational view egressing material(s)/content(s) by manual manipulation as would be carried out with a rigid housing enclosure/barrier structure 1 or by internal pressure increases and volume reduction with a compressible housing;

FIG. 3 is a front elevational view of the enclosure/barrier structure ingressing material(s)/content(s) via means of the enclosure/barrier structure wall springing back to initial position after compression;

FIG. 4 is a front elevational view of the enclosure/barrier structure having been emptied of prior material(s)/content(s), and showing returning the cap/closure back onto the enclosure/barrier structure;

FIG. 5 is an elevational view of an adapter for making a one-to-one passageway communication between a tubing/conduit and the enclosure/barrier structure;

FIG. 6 is an elevational view of a one to four adapter for making a passageway communication with a tubing/conduits and the enclosure/barrier structure; and FIG. 7 is aside elevational view of the enclosure/barrier structure having multiple passageway connection sites for drawing and creating expelling.

DESCRIPTION OF THE PREFERRED EMBODIMENTS

The method and apparatus for material(s)/content(s) management is disclosed in accordance with the present invention referring to the various enclosure/barrier structure embodiments described herein each having/providing methods and/or apparatus for volumetric displacement and volumetric replacement of dissimilar materials, and volumetric displacement and volumetric replacement of materials of dissimilar origin. As shown in reference to FIGS. 1-7 cubic volumetric displacement and/or replacement of dissimilar materials of dissimilar origin are impelled/expelled and/or ingressed and egressed or egressed and ingressed in accordance with dynamic gradient systems associated with enclosure/barrier structure 1. Volumetric displacement and volumetric replacement of dissimilar materials and volumetric displacement and volumetric replacement of materials of dissimilar origin, occurs to and from and from and to an instance of use by ingress and egress and egress and ingress in association with any of the various means of atmospheric gradient pressures caused by position, orientation, manipulation, external force, co-active and conjunctive positive and negative atmospheric pressure changes, structural movement, and/or alteration of atmospheric pressure. This action takes place in association with any one of and/or plural combination of cooperative coaptation passageway communication/connection sites 5, 20, 24, and 28 as shown in FIGS. 1-7, to/with passageway connectors coordinated and integrated to/with passageway communications means allowing material(s)/content(s) ingress and egress and egress and ingress to and from and/or from and to the material(s)/content(s) enclosure/barrier structure management system and a desired site/source, instance of use, and the like for the delivery to and the delivery from the instance of use.

Figure 1:
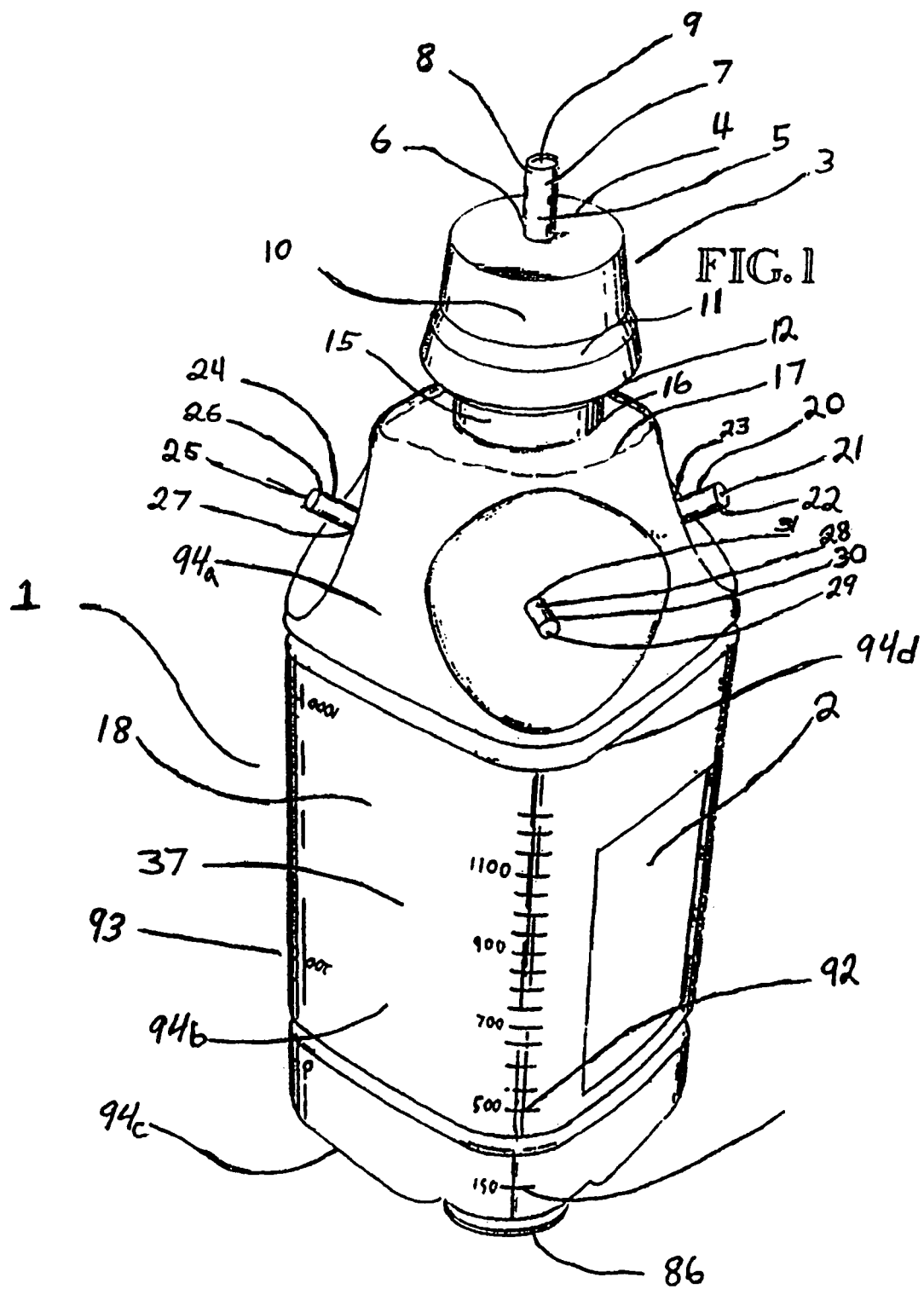

Referring to the embodiment of the invention shown in FIGS. 1-7, one can see demonstrated the methods and/or apparatus as illustrated in FIG. 1 includes the housing enclosure/barrier structure 1, which comprises the material(s)/content(s) enclosure. Housing enclosure 1 is hermetically sealed by a cap 10, which is attached at neck 15 the hermetic seal 12 being accomplished at interconnecting thread 11 (not shown). Housing enclosure 1 as illustrated in FIG. 1 is in an upright position having been filled with its initial sterile contents as shown by fill level 17. The housing enclosure 1, the filled fluid level 17, the cap 10 and the hermetic seal 12 being accomplished and carried out by one of and/or any number of combinations of manufacturing processes know by those skilled in the art for such processes. Housing enclosure 1 and cap neck 15 are joined integrally at 16. It is understood that the juncture which join's housing enclosure 1 and neck 15 may be rounded at 16 or may be filleted at 16 to accommodate a manufacturing processes for smoother production. Housing enclosure 1 also comprises one or more passageway communication/connection sites 20, 28, 24. Passageway communication/connection sites 20, 28 and 24 each comprise a hollow tubular formed passageway association each having a lumen of different inside diameter dimensions for the passage of different materials which pass in a different condition in different situations. Each of the different sized passageway communication/connection sites 20, 28 and 24 are integrally associated with housing enclosure 1 at 23, 31, and 27. It is understood that the configuration of the junction site between the passageway communication/connection 20, 28 and 24, is made integral with housing enclosure 1, may be radiused or filleted at 23, 31 and 27 to accommodate smoother easier manufacturing. It is understood that the outside diameter and the inside diameter of the lumens of passageway communication connection sites 20, 28 and 24, are sized and shaped to connect to and/or be associated with passageways by means of male to female fit of female to male fit. Passageway communication/collection sites at 20, 24, and 28 and 5 may also be of inverted female type extending into and below the surface of housing enclosure 1, and cap 10, in some instances. The ends of passageway connection sites 20, 28, and 24 have areas 22, 26, and 30 which defines and area for accessing and have ends 21, 29 and 25 which defines areas for accessing by spiking and/or piercing and the like. It is understood that the length, width, size and shape of the passageway communication/connection sites may be modified for a particular purpose yet still fall within the scope and utility of the present invention. Cap 10, is threaded onto housing enclosure 1 at neck 15. Cap 10 has a passageway communication/connection 5, which is integrally associated with cap end 4 at junction 6. It is understood that junction 6 ill its configuration and shape may be radiused or filleted for smoother manufacturing processes if necessary. Passageway communication/connection site 5 is shown generally as a male access. It is understood that communication/connection site 5 may take the form of a female access site which is formed and shaped below or deep to the surface of cap end 4. Cap 10 may also comprise within it a filter 3 (not shown) of sorts. Passageway communication/connection 5 comprises a longitudinally shaped hollow tubular passageway of sufficient size, structure, configuration and shape to pass material(s)/content(s). Passageway communication/connection 5 comprises an inside lumen 7 with an inside diameter of sufficient size for the passage of material(s)/content(s), which may be formed in different conditions. Passageway communication/connection site 5 comprises an area 8 for accessing cutting and an end area 9, which is suitably constructed for spiking, piercing, cutting. The inside diameter and outside diameter dimensions of passageway communication/connection 5 are suitably sized for association with passageway communication/connection by way of male to female, or female to male fit and male to female and female to male fit in two dynamic dimensions as both an externally projecting access site or an internally projecting access site. It is understood that end 9 of passageway communication/connection site 5 may be rounded or radiused for smoother manufacturing processes. It is also understood that passageway communication/connection sites 20, 28, 24 and 5 may be changed or modified for better manufacturing and/or better/easier connectability and suitability for end use. For example passageway connection site 28 is directed with a suitably horizontal projection with respect to housing enclosure 1. This is done to accommodate a tooling parting line that would symmetrically bisect passageway communication/connection sites 20 and 24 along a plane which is perpendicular/normal to passageway communication/connection site 28, the tool parting line passing through the centers of passageway communication/connection site 20 and passageway communication/connection site 24. It is also understood that with respect to an upright orientation for example, the various passageway communication/connection sites of FIGS. 1-7 may be directed vertically, they may be directed horizontally or they may be positioned at various locations with and among housing enclosure 1 and cap 10 without departing from the intended scope of the present invention. It is also understood that the passageway communication/connections sites may be everted (as shown) or inverted (not shown) with respect to the surface contours of housing enclosure 1. Housing enclosure 1 of FIG. 1 may embody sufficient structure and configuration such as in 94a, 94b, 94c and 94d, in both material and shape in having a wall thickness suitable for a rigid characteristic. The embodiment of FIGS. 1-7 defines housing a housing enclosure having rigid properties and characteristics. The present invention as described in FIGS. 1-7 has a rigid structure suitable for and sufficiently strong to resist collapse under gradient atmospheric ratio pressure changes, positive and negative both inside and outside of the enclosure 1, the structural characteristics of 94a, 94b, 94c, and 94d having a stable property which is greater than the pressures induced thereupon and there within by the alterations in positive and negative atmospheric pressure changes combined with the ingressing and egressing and egressing and ingressing of material(s)/content(s).

Figure 2:
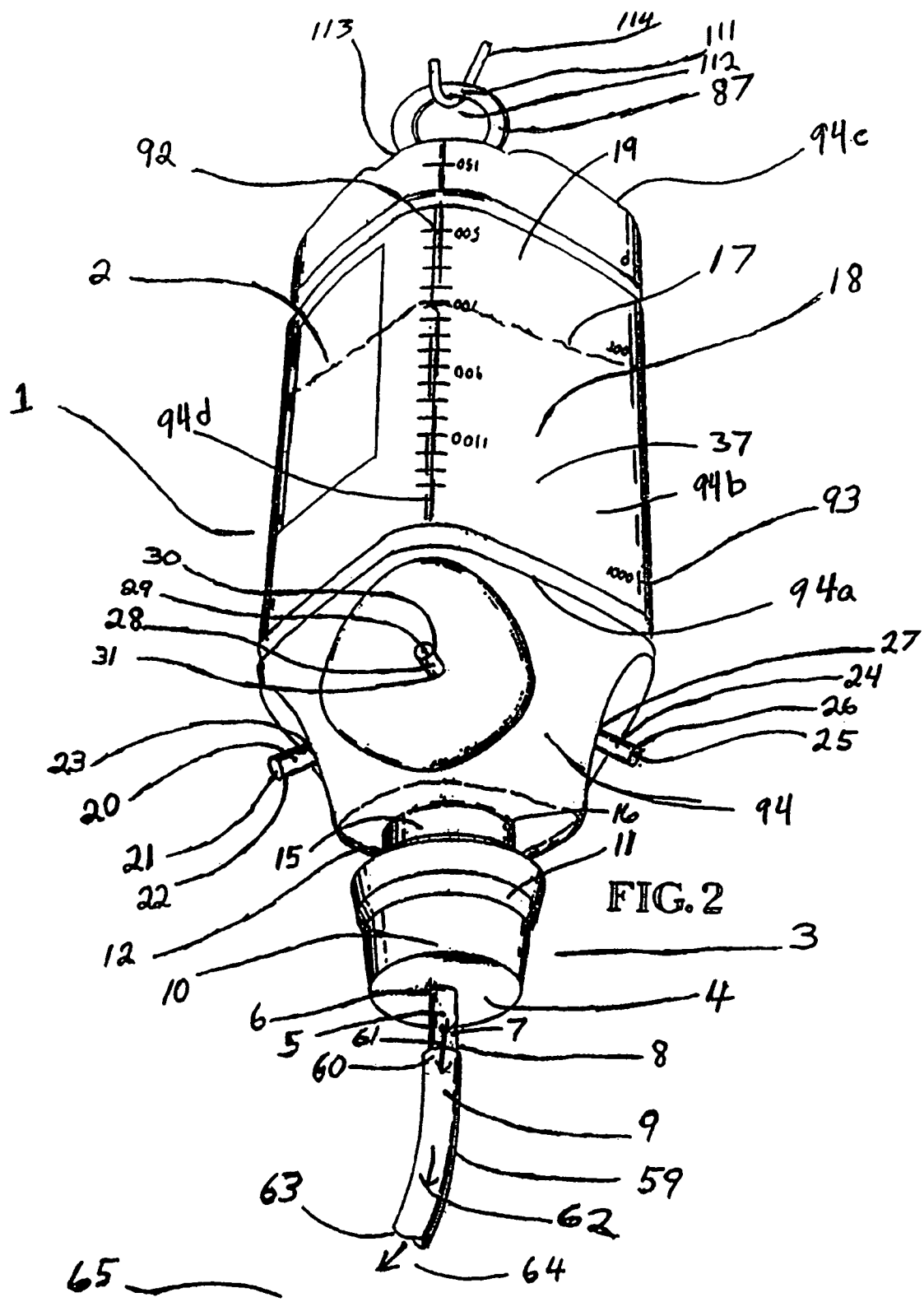

Housing enclosure/barrier structure 1 comprises a relatively thin walled structure 18 having an inside 37 for holding and containing the material(s)/content(s): Housing enclosure 1 is sufficiently marked with incremental unit indicator 92 and incremental unit indicator 93. Incremental unit indicator's 93 and 92 are reciprocally marked one inverted from the other so that changes in material(s)/content(s) levels of housing enclosure 1 may observed in both an upright position as shown in FIG. 1 as well as an inverted position as shown in FIG. 2. Housing enclosure 1 also comprises a labeling area 2 located on the housing structure for sufficient labeling. Housing enclosure 1 also comprises at one end a ringed aperture 86 shown here in a position flush with the bottom of housing enclosure 1. It is also understood that housing enclosure 1 is not restricted to the structural configuration as shown here, rather, the intended scope of the present invention includes a housing enclosure which may be modified in height, length and width without departing from the scope of the present invention. Likewise, the orientation of passageway communication/connection sites 20, 28, 24 and 5 may be, modified with respect to their orientation with and to the housing enclosure's height, depth and width without departing from the scope of the present invention. It is also intended that the orientation of the projection of passageway communication/connection sites 5, 20, 28 and 24 may be modified to accommodate tooling used in manufacturing process for the purposes of better tool removal, as well as lower manufacturing costs. It is also understood that the external configuration and contours of enclosure 1 including the contours at 94*a*, 94*b*, 94*c* and 94*d* and other areas of housing enclosure 1 may be modified for smoother manufacturing tool removal, lower manufacturing cost, and/or more ergonomic end use extended purpose applications.

In reference to FIG. 2, housing enclosure/barrier structure 1 is shown in an inverted position by hanging from hook 114, by means of placing hook 114 through aperture 112 of ring 111. Ring 111 is integrally connected with housing enclosure 1 at 113 at the base of housing enclosure 1. Passageway connector 59 is shown connected to passageway communication/connection site 5 by sliding passageway connector 59 over passageway communication/connection site 5 at 60. Prior to placement of passageway connector end 60 onto passageway communication/connection site 5 has been accessed, cut or snipped at 8 or spiked at 9 to create the open passageway communication connection. Passageway connector end 60 fits snugly over passageway communication/connector site 5 at 61 sufficient to create a leak proof seal as material(s)/content(s) egress occurs from within housing enclosure 1 out through passageway connector 59 along arrows 7, 62 and 64. Passageway connector site 59 comprises an inside lumen 63, which allows for such passage egress of material contents to a source of treatment/care 65. Alternatively, passageway communication/connection site 28, 20, and 24 could be similarly accessed, cut, snipped, spiked or pierced in preparation of the communication pathway site for pathway connector 59. In this particular instance passageway communication/connector site 5 at cap 10 is desired for use. In this instance volumetric material(s)/content(s) displacement shown at fill level 17 occurs via connector 59 along arrows 7, 62 and 64 through lumen 63 by means of gravity and/or may be assisted by means of mechanical control and/or a rate/dose regulation means which may be associated with connector 59 located between housing enclosure 1 and source of treatment/care 65.

Figures 2A, 3:
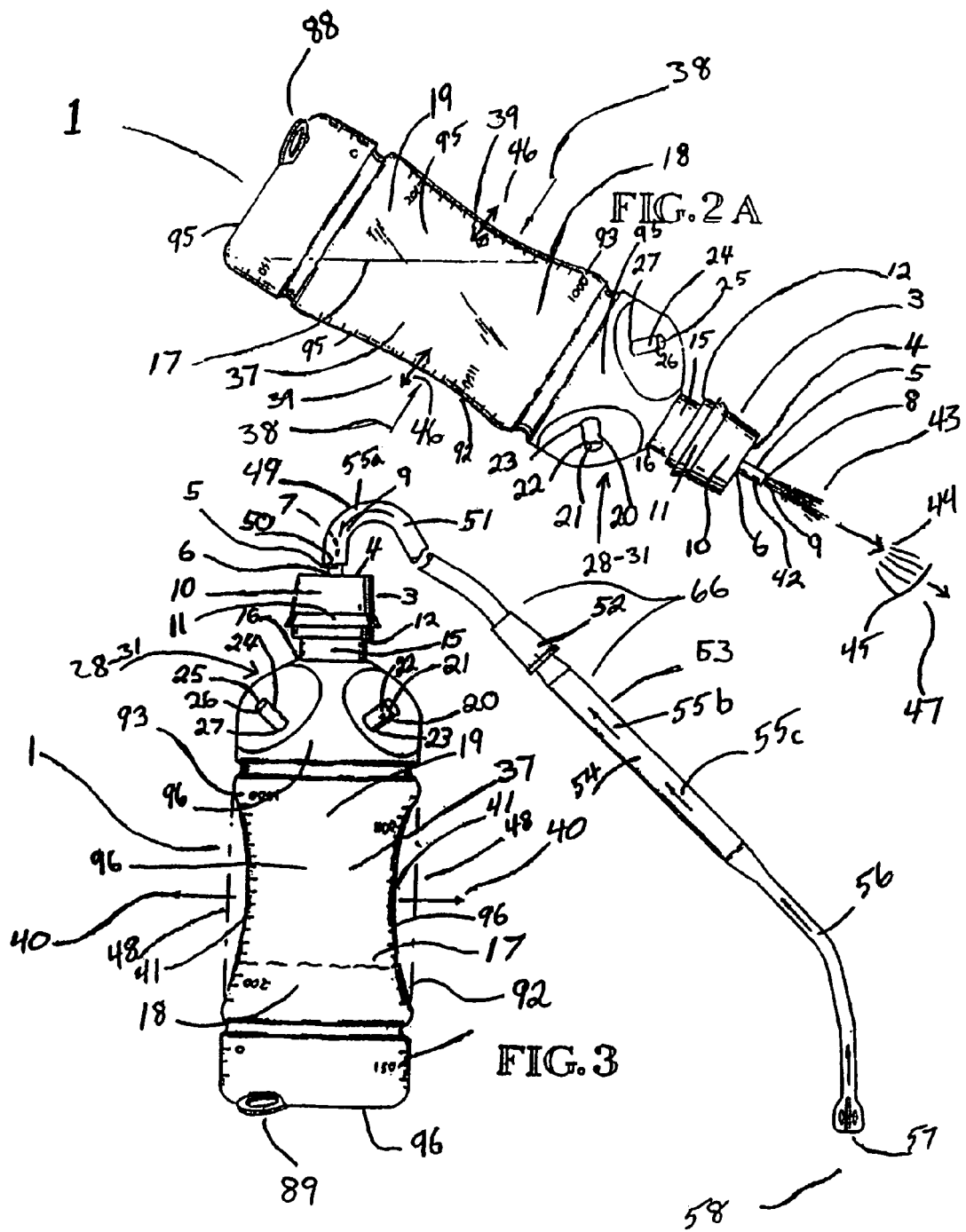

Referring to FIG. 2A, housing enclosure/barrier structure 1 is shown in a tilted position. Passageway communication/connector 5 has been accessed, cut, snipped, pierced or spiked at 8 allowing egress of material(s)/content(s) through opening 9. Material(s)/content(s) 43 and 44 is shown being squirted, sprayed and/or pulse lavaged along direction 45 to intended site/source of treatment/care 47. Volumetric material(s)/content(s) displacement is shown at fill level line 17. Material(s)/content(s) egress 43 and 44 occurs through opening 9 at location 8 on passageway communication/connection site 5. Material(s)/content(s) egress occurs as a result of housing enclosure 1 position or manipulation by means of gravity and/or force. Alternatively material(s)/content(s) egress may occur via passageway communication/connection site 24, passageway communication/connection site 20, and/or passageway communication/connection site 28. It is understood material(s)/content(s) egress may also be carried out by removal cap 10 from neck 15 by unthreading. In this instance volumetric material(s)/content(s) displacement would involve egress of material(s)/content(s) from neck 15 by simple tilting of housing enclosure 1 and pouring material(s)/content(s) from housing enclosure 1 to a desired site/source of treatment/care. It is understood that in the embodiment and use of FIG. 2A that usage of embodiment 2A on a sterile surgical field would require subsequent sterilization of the entire embodiment in order to be suitably clean for handling in a sterile field environment. In the instance of use and handling in a sterile field environment the embodiment of FIG. 2A would be subsequently sterilized in a peel pouch or a blister pack with a Tyvek peel cover and delivered to the sterile field as commonly practiced. The embodiment of FIG. 2A in an instance where subsequent use as a receptacle would be desired, the embodiment could be suitably shrink wrapped with a thin protective layer for handling during surgical use and then the shrink wrap removed for extended use purposes of the embodiment of FIG. 2A making it suitable for leaving the sterile field environment with the wrap removed providing a clean underneath embodiment surface for handling away from the sterile environment. Alternatively, embodiment 2A could be placed in a suitable small sterile wrap on the sterile field, which would protect it from contamination during use on the sterile field. Once use on the sterile field was complete the small plastic sterile wrap could be removed which would provide the clean uncontaminated surface of the embodiment suitable for transport and use away from the sterile field thus preventing/reducing carrying of contaminants out of the surgical suite. This describes another method of use, and extended purpose utility of the embodiment wherein housing enclosure 1 would function as a receptacle in an extended use fashion, reducing the number of container required in daily treatment/care practice.

In reference to FIG. 3, housing enclosure/barrier structure 1 is shown in an upright position having a connector 51 attached to passageway communication/connection site 5. Connector 51 is shown as being flexible at 49 and having end 50 forming a snug fit over passageway communication/connection site 5 forming an open communication between connector 51 and housing enclosure 1 through accessed end 9 of passageway communication/connection 5. Open lumen 7 defines the open passageway communication between housing enclosure 1, connector 51 and material(s)/content(s) passageway apparatus 53. Material(s)/content(s) ingress into housing enclosure 1 from treatment care source 58 flow and follow along arrow 56, 55*c*, 55*b*, 55*a*, through material(s)/content(s) passageway apparatus 53 through passageway connector 51 and ingressing into housing enclosure 1. Volumetric displacement within housing enclosure 1 is shown at material(s)/content(s) fill level 17 of which measurement may be observed at incremental unit measurement reading 92. Material(s)/content(s) may be ingressed into housing enclosure 1 from source 58 by means of gravity, by means of siphon or by means of other artificial mechanical assisted methods. In the instance of a siphon example connector 51 would be of extended length and the position of housing enclosure 1 would be substantially lower than the site of treatment/care 58. It is understood that connector end 50 of connector 51 may similarly be associated with housing enclosure 1 at passageway communication/connector site 20, 24, and or 28 (not shown). It is also understood that connector 51 and material(s)/content(s) passageway apparatus 53 may comprise any commonly used or new material(s)/content(s) passageway apparatus without departing from the scope of the present invention. For example a material(s)/content(s) passageway apparatus 53 may comprise a commonly used or new wound drainage catheter, a commonly used or new urine/bladder drainage catheter and the like. Other commonly known communication passageway apparatus and connectors such as shunts, stents, and other material(s)/content(s) carriers may be used without departing from the scope of the present invention. It is also understood that proprietary apparatus may be used, as shown at passageway apparatus 53 for the purposes of material(s)/content(s) ingress into housing enclosure 1 by suitably connecting and/or causing material(s)/content(s) passageway, for example between source 58 and housing enclosure 1.

Referring to FIG. 4, housing enclosure/barrier structure 1 is shown in an upright position. Cap 10 may be threaded onto neck 15 as directed by arrow 73 by rotational engagement between internal thread 13 of cap 10 and external thread 14 of neck 15. The engagement and seating of cap 10 onto neck 15 thusly recreates an airtight leak proof seal sufficient for containing material(s)/content(s). Housing enclosure 1 received material(s)/content(s) via ingressing through passageway connector 67 whereby passageway connector end 68 is in common connection with passageway communication/connector site 5. The interconnection between passageway connector end 68 and passageway communication/connection site 5 is achieved by a snug leak proof fit at 69. Accessed, cut or snipped end 8 and open end 9 of passageway connector site 5 defines the open communication pathway for enclosure housing 1 to receive material(s)/content(s) ingressed via lumen 70 of connector 67 along arrow pathways 71 and 73. The material(s)/content(s) 18 ingressing into housing enclosure 1 from the source of material(s)/content(s) 72. The material(s)/content(s) ingressing into enclosure 1 from source 72 may occur by means of gravity, excretion, secretion, oozing, bleeding, suctioning or by other artificially or mechanically assisted means. Volumetric displacement within housing enclosure 1 is evidenced by material(s)/content(s) at material(s)/content(s) fill level 17 the volumetric displacement level changing as a result in a alteration of the positive and/or negative gradient pressure ratios occurring from within housing enclosure 1 and/or by the ingress of material(s)/content(s) originating from source 72. It is understood that passageway connector 67 may be connected at one or more of the other passageway communication/connection sites at 20, 24 and 28 (not show) to carry out the effect of material(s)/content(s) ingress into housing enclosure 1 from source 72. Cap 10 may comprise there within a filter for purposes of trapping specimens, kidney stones or other material(s)/content(s) where it is desired to isolate or separate a portion of the material(s)/content(s).

Referring to FIG. 5, adapter 97 comprises an end 99 and an end 98 having open passageway communication there between at 99a. Ends 102a and 102b are sufficiently different in size such that either of size 102a or 102b may be sufficient for adaptation to passageway connection/communication sites 20, 28, 24 and/or 5. Thereby forming an adapter for non-like fitting connectors as might be found with connector 51 of FIG. 3, 67 of FIG. 4 or 59 of FIG. 2. The adapter of 102a or 102b may be planned to be adapted to any one of the sizes of the passageway connection sites and a differing sized passageway connector. The through passageway communicating there between body 99 and body 98 of adapter 97 is sufficiently patent and of a size to pass material(s)/content(s) without plugging or jamming. Adapter 97 may comprise therein a filter at 100 (not shown) for filtering, capturing or trapping specimens and the like. The filter may also act as a protector for maintaining cleanliness of suction tubes and the like which connect to a source of vacuum, suction pumping for drawing pressure out of housing enclosure/barrier structure 1. Adapter 97 may be used reversible as shown by arrows 101a and 101b for the purpose of ingressing and egressing and egressing and ingressing therebetween housing enclosure 1 of FIG. 4 and the source of material(s)/content(s) as in FIG. 4 at 72, FIG. 3 at 58, FIG. 2A at 47 and FIG. 2 at 65.

Referring to FIG. 6 adapter 103 comprises end 104 for connection with a passageway communication/connection site. Any one of passageway connector 105a, 105b, 105c, and 105d is sized and configured differently to engage and fit any one of the correspondingly different sized passageway communication/connection sites integral with/to housing enclosure/barrier structure 1, passageway communication/connector sites 20, 24, 28 and/or 5. Adapter 103 is configured as a one to four adapter having passageway communication there through between lumen 106a, 106b, 106c, 106d, by corresponding open communication with arrow 107, in correspondence with arrow 107a, arrow 107b, arrow 107c, and arrow 107d. It is understood that adapter 103 may be reversible or reciprocally used to interface between housing enclosure 1 and a source of material(s)/content(s) for ingressing and egressing and egressing and ingressing material(s)/content(s) between the source and housing enclosure 1.

Figure 7:
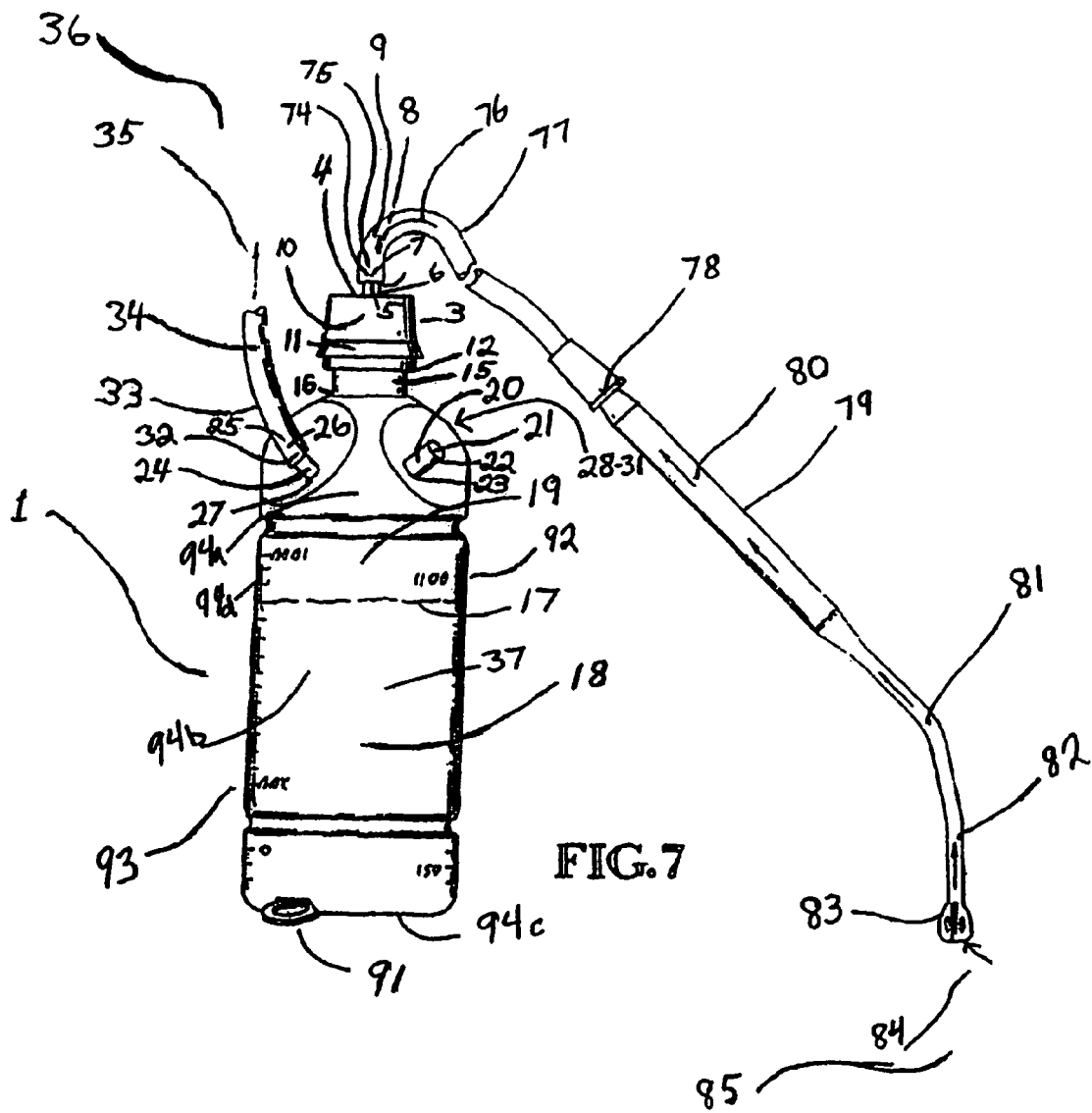

Referring to FIG. 7 housing enclosure/barrier structure 1 is shown in an upright position. In this instance material(s)/content(s) ingress into housing enclosure 1 from a source of material(s)/content(s) 85 via apparatus passageway 79 and passageway connector 77 is primarily affected by a vacuum suction draw at arrow 35 from an alternative vacuum suction pumping source 36. Passageway connector 33 is connected to passageway communication/connection site 24 by connector end 32 having a snug fit at end 26 of passageway end 24. End 25 having been snipped at 26 thus creating open communication with inside lumen 34 of passageway connector 33 allowing drawing of vacuum pressure therethrough from the source via passageway apparatus 79, via passageway connection 77 through housing enclosure 1, out passageway communication/connection 24, through inside lumen passageway connector 33 along arrow 35 to vacuum suction pump draw source 36. The suction pump vacuum draw source 36 having a draw vacuum pressure sufficient enough to move material(s)/content(s) from source 85 into passageway apparatus 79 along arrows 82 and 80 through passageway connector 77 along inside lumen 76 along arrow 76, the vacuum suction pump draw 76 being sufficiently powerful enough to draw material(s)/content(s) into housing enclosure 1, the material(s)/content(s) 18 resulting in volumetric displacement as shown by material(s)/content(s) fill level 17. The magnitude of vacuum suction pumping draw along arrow 35 may vary according to a desired degree of suction vacuum pumping draw magnitude. It is understood that adapter 97 or adapter 103 of FIGS. 5 and 6 correspondingly may be used between any of the passageway communication/connection sites and suction vacuum pump draw 33 whereby the filter of adapter 103 or adapter 97 would be useful in maintaining cleanliness of connector 33 and vacuum pump suction source 36. It is also understood that any one of the passageway communication/connection sites 20, 24, 28 and 5 may be used for the communication to the source of suction, vacuum, pump draw, 36 and or the source of material(s)/content(s) 85. It is also understood that under certain circumstances the location position orientation and direction of passageway communication/connections sites 5, 20, 24, and 28 may be positioned and oriented to reduce the interference between the ingress pattern associated with the material(s)/content(s) coming into housing enclosure 1 from source 85 and the egress of vacuum suction pump draw pressure as originated from source 36. For example in some instance of higher magnitude suction vacuum pump draw pressure from source 36 it may be desirable to reverse passageway connector 33 and passageway connector 77 such that passageway connector 33 is attached to passageway communication/connection site 5 and passageway connector 77 is attached to passageway communication/connection site 24. This would attach the source of suction vacuum pump draw pressure 36 via connector 33 to a location on housing enclosure 1 at a level that is higher than the location on housing enclosure 1 whereby material(s)/content(s) is being ingressed. This may assist in maintaining the cleanliness of connector 33 up, into and through lumen 35 to source 36. Source of material(s)/content(s) 85 may comprise numerous sources of treatment/care. For example source 85 may comprise a surgical wound, an open would, an endoscopic/arthroscopic wound, a body opening or body cavity, a body orifice pharynx throat esophagus or trachea. Source 85 may involve a joint space, placenta sack, urinary bladder, vaginal, rectal/colorectal spaces, abdominal cavity or thoracic cavity or any other location where a source of material(s)/content(s) may be encountered for the purposes of the retrieval of material(s)/content(s) via suctioning, irrigation and aspiration. Also sources such as bone cavities, spinal column, cranial cavities, orbital cavities and other cavities used and associated with use and application of the present invention.

FIGS. 1-7 describe the present invention in combination and in conjunction with a method and apparatus having a rigid enclosure/barrier structure providing unitary variable cubic capacity, the utilization and application of that apparatus in all of the methods, forms and variation described herein. In the rigid form, housing enclosure/barrier structure 1 of FIGS. 1-7 interrelates with the ingress and egress and egress and ingress of material(s)/content(s) as described whereby the structural integrity of the overall housing enclosure 1 maintains its position throughout the variable functions and the plural purposes intended under the scope of the invention. Volumetric atmospheric displacement of material(s)/content(s) occurs by means other than associative and corresponding movement by the housing enclosure structure. Rather, the housing enclosure structure 1 remains rigid throughout performance. Other means such as position, gravity, manipulation, siphon, drainage and suction, vacuum pumping drawing and other factors which cause ingress and egress and egress and ingress with respect to housing enclosure 1 of FIGS. 1-7. The rate of change of material(s)/content(s) fill level 17 of FIG. 1. FIG. 2, FIG. 2A, FIG. 3, FIG. 4, and FIG. 7 depends entirely upon the selected course of treatment/care and defines the dynamic of ingress and egress and egress and ingress of material(s)/content(s) with respect to housing enclosure/barrier structure 1. Passageway connector 59 of FIG. 2, 51 of FIG. 3, 67 of FIG. 4 and 77 of FIG. 7 may comprise multi-lumen or plural lumen passageway connectors. Such multi-lumen and plural lumen passageway connectors may be intended for the simultaneous ingress and egress or egress and ingress of material(s)/content(s) in communication/connection with housing enclosure 1. One such example of this would be for mechanical or pneumatic powered pulse lavage. Another example of this would be for mechanical control of irrigation fluids used for arthroscopic surgery. The housing enclosure/barrier structure 1 described in FIGS. 1-7 may comprise a semi-rigid/semi-flexible housing enclosure/barrier structure having/providing unitary variable cubic capacity.

Referring to FIG. 1, housing enclosure/barrier structure 1 having/providing unitary variable cubic capacity has its corresponding integral parts are made from a semi-rigid/semi-flexible material. The semi-rigid/semi-flexible material having characteristics suitable for such manufacturing delivery and storage.

Referring to FIG. 2 wherein housing enclosure/barrier structure 1 having/providing unitary variable cubic capacity, has its corresponding parts made from a semi-rigid/semi-flexible materials. The semi-rigid/semi-flexible material is capable of manufacturing shipping and storage of material(s)/content(s). Housing enclosure 1 of FIG. 2 is made of semi-rigid/semi-flexible material and has characteristics to maintain its structural integrity while inverted and egressing material(s)/content(s).

Referring to FIG. 2A, housing enclosure/barrier structure 1 having/providing unitary variable cubic capacity is made from a semi-rigid/semi-flexible material. Housing enclosure 1 being made from a semi-rigid/semi-flexible material will have spring like pliancy. Squeezing or applying external pressure to housing enclosure 1 at 39, and then releasing such pressure will cause movement of the housing enclosure wall 1 at 38. Squeezing and releasing and squeezing and releasing will cause movement of housing wall 1 as shown at 46. Subsequent additional squeezing and releasing and squeezing and releasing along housing enclosure 1 at wall 38 causes internal enclosure pressure fluctuations enacted upon material(s)/content(s) 18. When housing enclosure 1 is tilted as shown in FIG. 2A and one of the passageway communication/connection sites such as 5 has been snipped or cut at 8 creating the opening 9 pressure fluctuations 46 created by wall movement at 39 results in material(s)/content(s) egress 43 and 44 in a pulse lavage type of action. Such pulse lavage irrigation action in this instance in intended for a source of care treatment 47. The pliancy of housing enclosure 1 at wall 39 results in a spring back effect as a reaction to squeezing 38 resulting in a wall movement 46 in both in and out directions as shown, 46 defining the in and out motion of housing enclosure 1 wall at 39. The in and out action/reaction motion at wall 39 of housing enclosure 1 affects a pulse lavage irrigation egress of material(s)/content(s) action 43 and 44 which is similar to that enacted by the use of bulb syringe irrigating. FIG. 2A shows housing enclosure 1 tilted such that pulse lavage irrigation 43 and 44 may be affected by housing wall movement 46 at wall 39 of enclosure 1 the material(s)/content(s) fill line 17 showing a change in material(s)/content(s) fill level at 17. Material(s)/content(s) 18 egress may continue at opening 9 via pulse lavage 43 and 44 until housing enclosure 1 is emptied of its material(s)/content(s).

Referring to FIG. 3 wherein housing enclosure/barrier structure 1 having/providing unitary variable cubic capacity, is made from a semi-rigid/semi-flexible material. The housing enclosure 1 is shown FIG. 3 in an upright position. Referring to FIG. 3 whereby housing enclosure 1 is connected to passage connector 51 at passageway communication/connection site 5 at passage connector 50 wherein a snug leak proof connection is made at passage connector end 50 and passageway communication/connection site 5. In the instance of usage in accordance with FIG. 3 material(s)/content(s) at source 58 is drawn through passageway apparatus 53 along arrows 55c, 56, 53 and continues to be drawn along arrow 55a through passageway connector 51 and into housing enclosure 1. The material(s)/content(s) suction vacuum draw pressure, the negative atmospheric pressures created within housing 1 is generated from having first reduced the internal cubic volume of housing enclosure 1 by having squeezed in the sides of housing enclosure 1 at 41. Embodiment of FIG. 3 of housing enclosure 1 having been made from a semi-rigid/semi-flexible material which is spring pliant and has some return memory characteristics returns to its original cubic volume as shown by arrows 40 thus creating the suction vacuum and draw force which urges the material(s)/content(s) to pass from source 58 into passageway apparatus tip 57 along inside lumen 56 along arrows 55c and 55b up passageway apparatus 53 through interconnection at 52 between passageway connector 51 and passageway apparatus 53 along arrow 55 aid down through the open communication between passageway communication/connection site 5 and passageway connector 51 and then into housing enclosure 1. This squeezing and drawing action may be repeated a number of times. Volumetric displacement of material(s)/content(s) by an ingressing of material(s)/content(s) into housing enclosure 1 is illustrated by material(s)/content(s) fill level line 17. During the sequence of reducing the interior cubic volume of housing enclosure 1 by compression of the housing wall at 41 a disconnection between connector 51 and passageway communication/connection site 5 and or connector 51 and passageway apparatus 53 may occur to allow venting of air escape during compressing of housing enclosure 1 at 41. Once the volume has been reduced the aforementioned connections are re-connected and the suction draw urges material(s)/content(s) along arrow 56, 55c, 55b and 55a ingressing material(s)/content(s) into housing enclosure 1. It is understood that passageway apparatus 53 may comprise any number of commonly used, or new passageway apparatus. The selection of the passageway apparatus may depend upon what type of treatment/care is at hand, the nature of the material(s)/content(s) source and the environment of use involved with the course of treatment/care. It is also understood that passageway apparatus 53 and passageway connector 51 may be associated with housing enclosure 1 at any one or more of the passageway communication/connection sites 20, 24 and or 28. The functional aspect of FIG. 3 is not dependent upon which passageway communication/connection sites the passageway connector or the passageway connector apparatus is used in association with. It is also understood that because of the self enacting pressures of housing enclosure wall 1 urging the flow of material(s)/content(s) ingress into housing enclosure 1 that it is not necessary for die embodiment of FIG. 3 to operate in an upright position. Rather the embodiment as just disclosed in FIG. 3 may operate functionally in a tilted or sideways position. It is also understood that FIG. 5 and FIG. 6 function in like manner as previously described. It is also understood that the adapter of FIG. 5 and the adapter of FIG. 6 may be used correspondingly in like manner with the embodiments previously described for the rigid wall embodiment.

Referring to FIG. 7 wherein housing enclosure/barrier structure 1 having unitary variable cubic capacity, is connected to a source of vacuum suction pumping draw 36 by passageway connector 33 in open communication association with passageway communication/connection site 24. Material(s)/content(s) from source 85 is drawn up through passageway apparatus 84 through lumen 83 along arrow 82, 81 and continuing through passageway apparatus 79 along arrows 80 through connector junction 78 along through passageway connector 77 along arrow 76 through passageway communication/connection site 5. Connector end 74 of passageway connector 77 forms a snug leak proof seal at passageway communication/connection site 5. Suction vacuum pump draw pressure at arrow 35 from suction vacuum pump 36 draws material(s)/content(s) from source 85 into housing enclosure 1. Volumetric displacement of material(s)/content(s) from within housing enclosure 1 is shown at material(s)/content(s) fill level line 17. It is understood that it may be desirable to switch suction vacuum pump connector 33 and passageway connector 77. This would be done in an instance where it is desirable to have the source of pressure/draw/egress outlet located at a point on housing enclosure 1, at a level equal to or at a higher location on the enclosure wall 1 with respect to the inlet location on housing 1 where material(s)/content(s) may ingress rapidly and with force from the source 85. It is understood that the source of suction vacuum pump pressure egress draw output 36 and the source of material(s)/content(s) 85 may each be connected there between by the corresponding passageway communication/connection as described to any one of the passageway communication/connection sites 5, 20, 24 and 28 associated with housing enclosure 1. It is also understood in the instance of usage disclosed in FIG. 7 wherein housing enclosure 1 comprises semi-rigid/semi-flexible material, that the ability for the wall structure to resist deformation under negative pressure is greater than the net sums of the negative forces generated by the suction vacuum pump draw egress force with the material(s)/content(s) suctioned vacuumed pumped drawn ingress pressure forces combined. This insures that the housing enclosure 1 does not collapse with the changes of the combined atmospheric pressured encountered during operation.

In referencing FIGS. 1-7 showing drawings depicting volumetric displacement and volumetric replacement of dissimilar materials and depicting volumetric displacement and volumetric replacement of materials of dissimilar origin between the figures, wherein like numerals represent like parts, particularly pointing out distinctions between the rigid, semi-rigid, semi-flexible and flexible material embodiments.

The housing enclosure/barrier 1 having/providing unitary variable cubic capacity, may also be made from a pliant and flexible material. In this embodiment the structural position of the walls of housing enclosure 1 generally moves in conjunction with the ingress and egress levels/rate of material(s)/content(s). In a flexible housing enclosure such as in an intravenous bag/container or a commonly used container for arthroscopic irrigation the wall structure is bloated with the fill of its material(s)/content(s). The housing enclosure falls/collapses in response to the egress levels of its material(s) content(s). Referring to FIG. 3 housing enclosure 1 has associated with it a rigid or semi-rigid top comprising passageway communication/connections 5, 20, 24 and 28. Material fill level line 17 show material(s)/content(s) 18 at a low level within housing enclosure 1. Housing wall 41 shows a collapse corresponding to a low level of material(s)/content(s) 18 at material(s)/content(s) fill level 17. It is commonly know in the field that many intravenous solution bags, large and small parenteral solution bags, and irrigation solution bags collapse in conjunction with egress of its material(s)/content(s) and correspondingly may expand with the ingress of material(s)/content(s). Although the referenced drawing herein of FIGS. 1-7 do not specifically show the invention carried out using a standard commonly known type of flexible intravenous solution bag or a standard known type of flexible arthroscopic irrigation solution bag, there are instances where such housing enclosures/barrier structures of this type would be suitable for fitting and adapting of the necessary communication/connection sites, and communication passageways for carrying out the utility of the present invention, whereby the enclosure/barrier structure(s) having unitary variable cubic capacity function for the utility for reducing containers, reducing inventory, reducing medical waste, reducing waste in general, and the reduction of costs associated with the practice of treatment/care as disclosed by the present invention. It is therefore intended that the scope of the present material(s)/content(s) management method and apparatus invention will apply to flexible material(s)/content(s) enclosure/barrier structured containers as well.

It is also understood and known by those skilled in the art for surgical practice, that any cutting, snipping, or piercing or spiking of passageway communication/connection sites 20, 24, 28, and 5 must be carried out using implements which are previously sterile to prevent contamination of the passageway communication/connection sites. Sterile implements are readily available for use. It is also understood that the intended scope of the invention disclosed and referenced in FIGS. 1-7 that the appearance and style of housing enclosure(s)/barrier(s) structure(s) 1 may be changed without losing the utility of the invention, and without departing from the scope of the invention. For example the housing enclosure(s)/barrier(s) stricture(s) 1 may take the appearance of a commonly know receptacle provided for material(s)/content(s) ingress provided that such housing enclosure 1 in this instance is formed, filled and sealed appropriately to carry out the utility, processes and principles disclosed by the present invention. Such style could take the form and appearance of a suction canister, a wound drain reservoir, a urinary drainage bag or a number of different types of specialty bag enclosures or appear like common large or small parenteral solution enclosure/barriers.

The utility/object of the present invention is not dependent upon any particular size. Rather the scope of the invention is intended for sizing fitting and matching various applications in a variety of sizes, of which sizes meet the requirement of a plurality of purposes having/providing for various cubic capacity needs. There are a variety of functions, and a plurality of purposes whereby container(s)/package(s) material(s)/content(s) volumes (cubic capacity) differ for satisfying different needs. Applications whereby smaller material(s)/content(s) volumes, generally in the range of 50 ml and smaller and up to 250 ml for small volume parenteral solution enclosure/barriers, a pediatric, neo-natal, infant, or maternity/delivery ward where the use of the present invention will also have utility in smaller volume sizes and cubic capacity matching and fitting between instances of use, along with other sizes such as unit dosing, or sizes commonly found with volumes related to a variety of syringe size delivery of products. In contrast, use of the present invention in larger volume sizes substantially in the range where 3000 ml to 5000 ml of material(s)/content(s) may be packaged/contained for irrigation procedures for Arthroscopic and Urology procedures. The intended scope of the claims intends to cover all volumes where material(s)/content(s) are managed in enclosures, and to meet the requirement of material(s)/content(s) usage in volumes as required. The intended object of the present invention is also not limited to the relationship of the ratio of volume of material(s)/content(s) contained to the volume of the container/package provided. Instead, the scope of the invention is also intended to package volumes of material(s)/content(s), in package sizes whereby the intended extended use of the package, is desired and selected on the basis for an extended use purpose(s), including thermal therapy.

Shape

The utility/object of the present material(s)/content(s) management invention is not directed solely by its shape. Certain enclosure/barrier structural shapes may be more suitable for carrying out the utility of the present invention, or may have better use with or apply towards and together with various treatment modality/indication applications for further advantages as taught herein. For example, generally square, rectangular, narrow, oblong or other anatomically shaped embodiments of the material(s)/content(s) management invention may present more ergonomic appropriateness for certain applications. Thus, the utility of the present container(s)/package(s) invention is not solely dependent upon its overall shape, and the intended scope of the invention will include many types of shapes and configurations which conform the a desired combination or sub-combination as used.

Fields of Use

The utility of the present material(s)/content(s) management invention will be found to be beneficial in the consumer, industrial, commercial, manufacturing, other, and medical, industries whereby traditional container(s), package(s), carton(s), may be configured, and/or used for extended use for a variety of functions and for a plurality of purposes that go beyond the traditional intended initial purpose. More specific areas of use for the invention in the healthcare and treatment areas include, but are not limited to: Hospital (both in patient and out patient), Outpatient. Ambulatory Surgery Centers. Rehabilitation Centers and rehabilitation treatment facilities and wards/wings, Tong Term Care Facilities, Nursing Homes, Convalescent Institutions, Home Health Care, Ambulatory, Physician and Practitioner Offices, Medic One, Aid Cars, Ambulances, Military Institutions, Mash and Field use and applications, Specialty Care Facilities such as Cancer Research Centers. Other types of facilities, and methods may be employed to deliver the invention for use. These include medical supply outlets, rehabilitation clinics, drug stores, and other retail outlets, where such related supplies are available. Also the present invention may be made available for purchase on the internet, and the world wide web for easy access to the consumer and other institutions whereby supply chain convenience is made available, and where treatment and care is provided and/or given or practiced and any other type of facility, and instance of use where multiplication of container(s)/package(s) may be reduced to save costs, and reduce waste and lower inventory etc., by practicing the invention, and methods as disclosed in the present applications.

Dynamic Inter-Function and Cooperative Coaptation

The container(s)/package(s) of the present invention has fitting/configuration sites for providing methods and apparatus for carrying out methods and functional purposes that include different dynamic events. These dynamic events include material(s)/content(s) filling material(s)/content(s) dispensing, material(s)/content(s) receiving, material(s)/content(s) egress by force, material(s)/content(s) ingress by force, material(s)/content(s) collection by internal suctions, material(s)/content(s) collection by external vacuum, a material(s)/content(s) reception by drawn atmospheric pressure, material(s)/content(s) receiving by gravity, manual ingress and/or egress applications of the material(s)/content(s), material(s)/content(s) ingress by shape memory, and the like. Also included is material(s)/content(s) circulation and mixing. The variable function, and plural process/method of the present material(s)/content(s) invention is suited for many extended use purposes which may include the management of, dealing with, treatment of, and disposing of, body secretions, body fluids, combinations of body fluids with other fluids, solids, liquid and gasses, carriers for absorption and transfer of thermal therapy, as well as many other extended uses. These extended uses are given to illustrate just some of the processes and methods which may be carried due to the utility of the present material(s)/content(s) invention of which scope(s) and embodiment(s) are intended for a plurality of purposes and variety of functions by way of/and interfacing with the container(s)/package(s) invention by way of association therewith, interconnection thereto, and interrelation thereupon and intercommunication there-between.

Fluent Material(s)/Content(s)

Material(s)/content(s) for the purposes of the present invention shall be defined as any combinations and sub-combinations, and composite combinations of/and all solids, liquids and gasses (matter) flowable, packagable, enclosable and containable material(s)/content(s) used and applied, controlled, received, circulated, re-circulated, replaced, heated, cooled, thermally treated, thermally applied, ingressed, egressed, dripped, pumped, vacuumed, pressured, forced, urged, controlled, managed, monitored, traced, tracked and/or disposed of in the course of care and treatment through collection and disposable in the medical field or any form or combination thereof. The package/container/enclosure may be hermetically sealed or sealed by other types of cap and closure, methods and apparatus. The enclosure/barrier of the present invention is interposed between the material(s)/content(s) and the environment to prevent the material(s)/content(s) from contacting the environment and to prevent the environment from contacting the material(s)/content(s). Materials(s)/content(s) may comprise tissues of the body and materials associated with a continuum of care. Tissue(s) for the purposes of this application shall mean any and all solids; liquids, gasses (matter) of the human, and animal, veterinary mammal and non-mammal body. This includes material(s)/content(s) that come in contact with the body, are inserted/integrated into the body by a variety of ways, and body tissue material(s)/content(s) that are also removed from the body in a variety of ways. Material(s)/content(s) shall also include any and all solids, liquids and gasses that are used in conjunction to facilitate use of apparatus involved in treatment/care, and the material(s)/content(s) that facilitates use of and management and care of apparatus used in such treatment/care. Also included are apparatus applications by-products such as smoke, and other by-products, which result from the application of radio frequency cautery devices, laser devices, thermal, ultrasonic, and harmonic cutting devices, as well as insulation gasses used to facilitate endoscopic surgery among other things. Also included are body tissues, placenta fluids, amniotic fluids and fluids and materials and tissues of the womb and giving birth, fluent materials associated with the care of newborns and premature infants, fluids and materials of/associated with the peritoneal cavity, fluids and materials of/associated with the vascular system (liver-gall bladder), fluent materials associated with the urinary system (kidneys, ureters, urinary bladder, urethra) fluent materials of/associated with the alimentary canal, fluent materials associated with the billiary system, materials associated with the respiratory system, fluids and materials of the lymph system material(s)/content(s) removed for further study (specimens) or body tissue material(s)/content(s) and fluids that are removed and readily disposed of, disintegrated obliterated enucleated and the like. Also included are blood, blood products, urine, cerebral spinal fluids, saliva, pus, mucus, mucus membranes and related secretions, abscessed tissue and fluids, inured tissue(s), damaged tissue(s), traumatized tissue(s), and other non-functional tissue(s). Material(s)/content(s) shall also include: disease(s), diseased body tissue(s), unhealthy body tissue(s), body tissue(s) deemed not desirable to remain in the body, excess body tissue(s), overabundance of body tissue(s), resected body tissue(s), infected body tissue(s), abscessed body tissue(s), body tissue(s) removed as a result of disease process integration, body tissue(s) determined to be a part of sickness or illness, tumors, cancers and the like, component(s) parts of body tissue(s). Also included are tissues-material(s)/content(s) that are associated with the use of robotic equipment, visual enhancement equipment of any kind such as using scopes, lenses and monitors, virtual reality visual assisted monitoring equipment and any other remotely applied machine vision or sensor based machinery and equipment. This invention may also have utility in the application of gene therapy, whereby any material(s)/content(s) are manufactured, distributed, used, collected and disposed. This list is not meant to limit the scope of application of the invention, rather to illustrate many of the examples. Material(s)/content(s) shall also include fluids and carriers of medicaments, dilettantes, saturants, and chemical combinations of pharmaceutical preparations. Material(s)/content(s) shall also mean insuflation gases in combination with body material(s)/content(s) and irrigation solution. This list is not meant to limit the scope of the invention, but rather to provide some examples of some of the material(s)/content(s) the invention is intended to be useful in managing/controlling. Furthermore, the scope of the invention is intended to have utility for the variety of dynamic situations, and plurality of purposes encountered in managing any material(s)/content(s) whereby the invention has utility, and is directed towards the coordination between enclosures and passageway connection means, reduction of containers, reduction of costs, and reduction of inventory used for daily operations in multiple settings where care and treatment is provided, in a way that results in Activity Based Cost reductions.

Cooperative Coaptation and Volumetric
Displacement and Replacement of Materials of
Differing/Dissimilar Origin having
Dissimilar/Differing Material Makeup Fitting association for the purposes of the present invention shall mean the various communication pathways by which material(s)/content(s) go to and from and from and to the enclosure/barrier-container(s)/package(s). Apertures, ducts, tubing's, conduits, mechanical assemblies machines, devices and the like comprise different fitting associations which make up passageway connectability coordinating the communicating with and the delivery and receiving of material(s)/content(s), and accessing the enclosure/barrier material(s)/content(s) management invention for different purposes. Fitting associations are utilized with rigid, semi-rigid, semi-flexible and flexible container/packages. Fitting association, as a part of the container(s)/package(s) utility, associates linkage/communication of the container(s)/package(s) invention and material(s)/content(s) to other receiving/delivery systems/tubing functioning as passageways thereby providing the object of linking and coordinating manufacturing, distribution, uses, application, collection and disposal into a new and novel coordinated system having the described labeling/indications. This linkage further integrates the invention's processes and methods to provide the objects of the functional composite combination system(s), thereby carrying out the object of treatment/care intended by association and interrelation with the container(s)/package(s) methods and apparatus of the present invention. Many prior art "traditionally indicated/labeled purpose" container packages are in use that have fitting associations whose functional utility are limited to the "initial indication/labeled purpose" of the container(s)/package(s). The present material(s)/content(s) management invention embodies different sized fitting communication/connections that are configured and constricted for plural coordinated purposes/use, in a fashion and configuration to be easily adapted and used for the plural indicated/labeled use and a plurality of additional purposes. The differently embodied extended use fitting connections may vary in size relative to the desired size of the overall container and the desired volume, but the variety of sizes of the extended use fittings allows communication/connection with/to systems such that the container/package functions suitably in an extended purpose capacity. The extended use communication/connection fittings also vary in size per each container so that the material(s)/contents will not become clogged or jammed along the passageway while traveling into or out of the material(s)/content(s) management invention. For example, one size extended use fitting may be suitable for the passage of fluids, while another larger size extended use fitting may be suitable for passage of a body tissue, which comprises pieces of solids. Such solid, or some semi-solid debris may comprise material(s)/content(s) such as bone debris, fat deposits, bone cement debris, body organ tissues, body tissues, or other types of material(s)/content(s) that travel along the tubing/conduit passageways in non-fluid forms or in conjunction with fluids and gasses. Such combinations of material(s)/content(s) will vary with each situation where the container(s)/package(s) invention is used. A container(s)/package(s) having a selection of different sized extended use communication/connection fittings allows the operating personnel to select the fitting that best accommodates the use at hand. The invention apparatus, methods, processes and utility extends beyond the container(s)/package(s) to the conduit(s), tubing(s), kits, and methods which are combined with the container(s)/package(s) utility to form the systems that carry out a variety of functions for a plurality of purposes newly indicated use connections comprise the conduits and passageways whereby the material(s)/content(s) may pass to and from and from and to the container(s)/package(s). The extended use connections are generally provided in the form of conduits, tubing(s) and passageway(s) which have end form configurations for association with the container(s)/package(s), or the material(s)/content(s) source, IE the body, a body cavity, a body organ, a body vessel, a body tissue, a body vessel/artery/vein a machine, and/or is affected commonly by another external or intermediary device which enacts upon the tubing/conduit/passageway for particular purposes. Extended use connections may be for purposes not only associated with insertion into the body, but may be utilized to be combined and associated with bandages, dressings, casting materials, splinting materials, bracing materials and external fixations devices and materials and the like for the purposes of ingressing and egressing radiant thermal temperatures for thermal treatment modalities (hot and cold therapy) and for pressure dressings/bandages and the like. Other extended use connections, fitting and intercommunication passageway means may be utilized for monitoring patient fluid volume levels. These extended use connections connect, combine and inter-associate the container(s)/package(s) to system(s) for performing operations/procedures that could take place for a variety of additional functions and additionally for a plurality of purposes. Use of a tubing/conduit is one of the common types of passageway link between elements of a system function. Tubing/conduit for the purposes of the present invention may be single lumen, double lumen, plural lumen, multi-lumen, or not necessarily lumenar, as one such example is found in wound drains that provide for flow but do not comprise and enclosed tubing/conduit per se, and/or the like. They may be congruent, composite, fitted/mated with the container/package to perform the extended use function(s) via any of the extended use communication/connection fittings. They may be a single length or may comprise a composite connection(s) that are configured for further convenient integration with systems such as the needle-less port systems currently available on the market. They may be in the form of a cassette or cartridge, or may associate with apparatus which impacts/controls the rate, flow, speed, pressure, force, temperature timing etc. of how the material(s)/content(s) passes along the passageway, or how the material(s)/content(s) is best controlled for optimal performance/safety within or outside of a body cavity, as such is appropriate when forcibly moving fluids/gasses into a body joint or cavities is carried out with arthroscopic surgery and endoscopic/laparoscopic/arthroscopic surgery, to give just a couple of example. These extended use connections must be suitably constructed with the strength and resilience to maintain functional integrity under suction, vacuum, pressure, mechanical contact as well as the abrupt stoppage of the aforementioned, and resist collapse under pressures used, and resist inflating under the pressures used. They may also be constructed to be enacted upon by intermediary devices which act upon the passageway means for particular passageway regulation or control. Another object of the invention is to provide methods and apparatus which may co-operate within an outer enclosure, or a shell that surrounds the material(s)/content(s) management enclosure in a rigid fashion with just enough structural strength to pass anti-implosion resistance to a flexible, semi-rigid, semi-flexible embodiment of the present invention. Another object of the invention is to provide methods and apparatus that may be coordinated, and linked electronically to use weights and measures to control information relating to the processes in surgery involving patient fluid volume tracking and treatment. The objects, and principles provided by the methods and apparatus of the present invention are intended to be incorporated, and inherently implied and to be applied in combination and sub-combination with the herein description(s)/heading(s) of Material(s)/Content(s) Ingress, and Material(s)/Content(s) Egress. For the purposes of any product and process association with the present invention, the descriptions and disclosures under all headings herein disclosed, and particularly the disclosures defined under the headings of Material(s)/Content(s) Ingress and Materials(s)/Content(s) Egress and Fitting Association and Pathway Communication Intercommunication are incorporated/integrated herein by reference and intended to be applied to and fall within the scope of the present invention in combination and sub-combination as defined by the principles of inherence. Similarly this application is intended to disclose the invention in its broadest form(s)/sense, and this application is not intended to limit the scope of the invention, or limit the intended broad scope by definitions of any particular terms, yet the objects, and the utility of the present invention are intended apply to all apparatus and methods, and combinations and sub-combinations as allowed by the attached claims.

Fluent Material(s)/Content(s) Ingress and Volumetric Displacement and Volumetric Replacement of Differing Materials Each having Differing Origin Impelling and expelling material(s)/content(s) by ingress is disclosed herein. The present container(s)/package(s) invention is fitted to receive material(s)/content(s) for a variety of functions, a plurality of purposes and in a variety of ways. Along the supply chain, from raw material to eventual disposal, the utility of the present invention is directed towards the reduction of multiple container(s)/package(s) receptacles/enclosures to reduce cost, and inventory and to provide methods and apparatus for a variety of treatment modality indications. The communication/connection fittings of the material(s)/content(s) management invention allow material(s)/content(s) ingress along the continuum of use now made available by the inventions unique design coordination and integration and novel uses configuration. Ingress of material(s)/content(s) may include a variety of methods, involve a variety of apparatus, and occur at a variety of times/instances up and down the useful life continuum of the container(s)/package(s) invention. Some of the container(s)/package(s) invention material(s)/content(s) ingress are included here for illustrating the utility of the invention. Some of these include initial filling. The instant container(s)/package(s) invention may be initially filled with material(s)/content(s) in a fashion as commonly practiced by the manufacturing community having skill in the art of forming, filling and sealing container(s)/package(s). These filling and sealing methods and apparatus for initial material(s)/content(s) ingress are mechanized and automated for low cost production of initial material(s)/content(s) ingress. The present container(s)/package(s) invention is well suited for such mechanized, automated high volume production ingress of initial forming, material(s)/content(s) filling and sealing. At the time of container(s)/package(s) production, the invention may also be fitted for access of an additive(s) means, say for example, a medicament for the treatment of disease, pharmaceutical preparation, antibiotic, or other chemical composition integrated into t cycle of treatment modality, or for the control of metabolic processes of body functions, or the control of infection, or to assist with the management of a pyrogenesis, etc. The additives may be co-mingled with the initial material contents at a later time, once the determination is made by the care giver as to what kind of additive, and dosage is necessary, or appropriate for the given situation. The container/package invention may be fitted so that dose specific additive(s) may be easily administered by volume and or concentration and/or in a timing regiment as determined by the care giver, prn. Additional material(s)/content(s) ingress may be carried out along the continuum useful life of the container(s)/package(s) invention by a variety of other methods and apparatus during treatment/care. Other container(s)/package(s) material(s)/content(s) ingress may occur by means as motivated by gravity, by body function control output, by body pressure, by vessel flow, by wound secretion, by organ emission of body materials, by the container(s)/package(s), memory characteristics after deformation, by vacuum, siphon, suction, or many other possible mechanical means. Other possible mechanical means may be in additional forms that may be integrated to regulate flow, pressure, rate etc. of the ingress of the material(s)/content(s) into the container(s)/package(s) invention. Material(s)/Content(s) may comprise medium for the controlling, carrying and radiating of thermal therapy treatments, and or for the purposes of providing controlled pressure in coordination with bandages, dressings, casting materials, splinting materials, bracing that is static or allows for range of motions, external fixation and the like along with other trauma related treatment modalities. This is not meant to be an exhaustive list of container(s)/package(s) material(s)/content(s) ingress, rather these are some of the many potential examples given in to demonstrate the novelty, utility, and versatility of the container(s)/package(s) invention, and in many ways describe the Utilitarian value by the potential to reduce multiplication of prior art containers, and the reduction of inventory and reduce costs along the supply chain while helping environmental concerns by reducing regulated and unregulated medical waste, and having a positive impact on the economics of the supply chain costs associated with the delivery, and use of products throughout health care treatment modalities.

The passageways for interconnection of the container(s)/package(s) with and to the source if material(s)/content(s) may take the form of tubing(s), conduits, congruent or composite methods and apparatus, etc., that have suitable characteristics to function appropriately to interrelate thereto, and inter-communicate there-between the source of the material(s)/content(s) and the enclosure/barrier container(s)/package(s). Such passageways may comprise a composite interconnection of methods and apparatus. Angio-catheters used for purposes such as Intravenous Starts, tubing, needles used for such IV start kits, blood collection, wound drains for draining postoperative and other wounds, Foley catheters, and other types of urinary bladder drainage catheters, peritoneal drainage conduits, cerebral/spinal fluid drainage, chest cavity drainage, other body organ or tissue material(s)/content(s) either in solid, liquid or gas form, or the like in combination with other types of solids, liquids and gasses whereby suction catheters and suction tubing conduits, passageways, and suctioning tips as well as aspiration/suction apparatus are used to manage material(s)/content(s) there-between the source and the container(s)/package(s). Irrigation/aspiration devices which are used in endoscopic/arthroscopic procedures used for facilitation of the procedure by the removal of body organ tissues along with operational material(s)/content(s). Other types of technological devices such as lipo-suction devices, ultrasonic devices, dissectors, shavers, scissors, cautery, forceps, tissue abators, radio frequency devices, lithotripsers, laser devices, electric, battery and pneumatic powered devices may all include operation with interconnecting passageways for the removal of solids, liquids and gasses for a variety of functions, and a plurality of purposes in removing and passing body tissues and other material(s)/content(s) between a source of material(s)/content(s) and a container(s)/package. This list is not intended to limit the scope of the present invention, rather this list is intended to illustrate some of the variety of functions and plurality of purposes for which the present invention has use, utility, and co-functional systems interrelation therewith. Such co-functional interrelation, and passageway communication may be established there-between by passageway end configurations comprising, angiocatheters, needles, spike, slip fit, male or female, leur lock, linear slide fit, threaded, press or slip fit, geometric shape fit, interlock, tubing, or any other composite means which appropriately will maintain the passageway communication/connection between the source of material(s)/content(s) and the container(s)/package(s) to carry out the intended function. Such passageway, and the movement of material(s)/content(s) between source and the container(s)/packages(s) may be for biopsy purposes, or may be controlled by/with image guided systems that integrate three dimensional images with devices for treatment and care via computerized image guided systems.

Fluent Material(s) Content(s) Egress and Volumetric Displacement and Volumetric Replacement of Differing Materials having Differing Origin Impelling and expelling Material(s)/Content(s) by egress is disclosed herein. Material(s)/content(s) egressing from the container(s)/package(s) invention may take form of a variety of functions for a plurality of purposes and in associations with numerous methods and apparatus. Such material(s)/content(s) egress may be regulated and or controlled in volume, rate, flow, force, pressure, temperature speed and the like. Material(s)/content(s) vary widely, and therefore cover a broad range of applications for the purposes of performing a variety of intended functions and for accomplishing a plurality of intended purposes. Such container(s)/package(s) material(s)/content(s) egress may occur by gravity, by an added pressure, by intermittent pressure, by manual pressure, by the control of a patient or other controlling factors. Furthermore, such container/package material(s)/content(s) egress may be regulated manually, by machine, by sensor, by computer, by pump, or other electronic, battery powered, pneumatically powered, portable or non-portable device, mechanical or otherwise to coordinate the rate, volume, dose, concentration and amounts of material(s)/content(s) egress together with the conditions of care which call for such application and use of the material(s)/content(s) egress. The container(s)/package(s) material(s)/content(s) egress may occur at multiple times along the useful life of the container(s)/package(s) invention, along the continuum of care, and may involve the egress of different material(s)/content(s), and different combinations of material(s)/content(s). Egress of material(s)/content(s) may also involve re-egress of the same, some of the same or of different portions. Combinations or percentages of the same, similar or mixed material(s)/content(s). This is provided that the container(s)/package(s) is handled in such a manner that is suitable for such purposes. Egress of materials(s)/Content(s) may comprise circulation and or re-circulation of thermally controlled medium for maintaining or changing the radiant temperature for application in "hot and cold therapy" applications. Egress of material(s)/content(s) may also include coordination with special systems that dispose of medical waste in fashions that reduce handling and reduce exposure risk of personnel and the environment to contaminants, embodied in the material(s)/content(s).

The passageways for intercommunication of the enclosure/barrier container(s)/package(s) with, to and from, and from and to the source of material(s)/content(s) may take the form of tubing's, conduits etc, and the like which have suitable makeup to function appropriately for the interrelation between, and the intercommunication between the source of the material(s)/content(s), and the container(s)/package(s) invention. Such passageways may be congruent, or may comprise a composite interconnection/combination of methods and apparatus. Angiocatheters used for the purposes such as starting intravenous solution treatments, tubing, needles and syringes used for such intravenous solution starts, blood collection, wound drainage and drain passageways for draining post-operative and other types of wounds, Foley catheters, and other types of urinary and bladder drainage devices, chest cavity drainage, other body organ drainage, or other removal of body tissue or operative tissue, in either solid, liquid and/or gas form, or a combination thereof, in combination with other types of solids liquids and/or gasses whereby irrigation/suction/aspiration and other types of conduit passageways and suction tipped methods and apparatus are used to manage material(s)/consent(s) between the source of the material(s)/content(s) and the container(s)/package(s). Irrigation/aspiration devices used in endoscopic/arthroscopic and other procedures, and other devices used for the facilitation of communication passageway for material(s)/content(s) between the source and the container(s)/package(s) for the purposes of management of the content(s)/material(s). Other types of technological devices such as lipo-suction devices, ultrasonic devices, laser's, mechanical, knives, cutters, baskets, dissectors, scissors, shavers, cautery, forceps's, lithotripsers, VTOP suction apparatus and the like, including electric, battery, pneumatic powered devices may all be used with and include interconnecting passageways for the delivery/removal of material(s)/content(s) in the form of solids, liquids and/or gasses including combinations thereof, for a variety of functions and for a plurality of purposes, acting in combination with such passageways and thereby intercommunicating there-between the source of material(s)/content(s) and the container(s)/package(s). Furthermore this list is not intended to limit the scope, application or use of the present material(s)/content(s) management invention, but to illustrate some of the variety of functions and plurality of purposes for which the invention may have use, utility, and a co-functional systems interrelationship with devices which provide/fix/prepare material(s)/content(s) for passageways from the source to the container(s)/package(s) and vice versa, in conjunction with the present invention, result in the reduction of the number of container(s)/packages(s) used, reducing the costs, and reducing the inventory and reducing handling required along the supply chain, for operations/procedures carried out along a continuum of care/treatment. Such co-functional interrelation, and passageway communication may be established between by passageway's having end configurations comprising needles, angiocatheters, tubing, introducers, spike, slip fit, male or female fit, leur lock, lock and lug, clockwise or counterclockwise, linear slide fit, threaded, Christmas tree type adapter, geometric shape fit or lock, snap fit, interlock, taper fit or any other means which appropriately will maintain the passageway communication between the source and the material(s)/content(s) enclosure/barrier-container(s)/package(s). Such passageway's, and the movement of materials between a source and material(s)/content(s) container(s)/package(s) may be for the purposes of biopsy, or may be controlled by image guided mechanisms and systems, that integrate three dimensional images for the purposes of carrying out procedures using devices for treatment and care using computerized image guided systems.

Impelling and Expelling Fluent Material(s)/Content(s) via Re-egress and Re-ingress and the Volumetric Displacement and the Volumetric Replacement of Differing Materials having Differing Origin The container(s)/package(s) invention material(s)/content(s) may involve re-egress and re-ingress of at least a portion/percentage of, if not all of the material(s)/content(s). This occurs for the purposes of re-circulation, re-cycling, or egressing what is ingressed or ingressing what is egresses and vise versa. The utility is for the purposes of re-using, or re-cycling material(s)/content(s) during a continuum of care, and how the material(s)/content(s) becomes associated with the container(s)/package(s) invention. This could involve material(s)/content(s) used for the purposes of thermal (hot or cold) therapy, re-infusion of blood, re-ingress or re-egress of other material(s)/content(s) used for irrigation purposes whereby initial purpose container(s)/package(s) typically dispense of such material(s)/content(s) in a fashion whereby the receiving receptacles are not suitable for economizing the material(s)/content(s). The act of the container(s)/package(s) functioning as a circulatory, cycling embodiment is additionally one of the many novel separate and unique utilitarian advantages of the present material(s)/content(s) management invention standing in as an extended use/value added container(s)/package(s) which can reduce the number of containers, reduce inventory and reduce costs along the supply chain involving the continuum of treatment and care.

Manufacturing Materials

The present container(s)/package(s) invention may be manufactured from a variety of readily available manufacturing materials used commonly for containment and packaging in the medical field to satisfy the rigid, semi-rigid, semi-flexible and flexible requirements. Such materials include resins like Polyvinyl Chloride, Thermoplastic Polyesters, fight Density Polyethylene, Polypropylene, Low Density Polyethylene, Polystyrene, Thermoplastic Elastomer's, engineered plastics and resins, silicones, Acrylic, Acrylonitrile-Butadiene-Styrene (ABS), Nylon, and the like. Other polymers and combinations of plastics may be suitable. The specific material which comprises the container(s)/package(s) invention ma) be different for a different desired extended end use. Glass is also used for the containing and packaging of medical material(s)/content(s). Manufacturing materials are available in bulk, and in sheets and strips, which may be joined at the periphery and closed. The intended scope of the present invention does not rely in particular on which material is selected for the container(s)/package(s) invention, rather any of the materials listed may be suitable provided however specific requirements of use along the continuum of care are considered in the selection of the actual material the container(s)/package(s) will ultimately be made from.

Manufacturing Methods

The container/package invention may be made using a variety of commonly known manufacturing machinery, and manufacturing processes. These processes include the use of blow molding equipment, automated filling equipment, blow fill seal machinery, form fill seal machinery, injection molding equipment, tubing/conduit extrusion machinery, and thermal/ultrasonic joining of composite plastic sheets, strips, foils or films of materials, joined at the periphery (with or without a joining medium (adhesive)) that can be made into container/packages, sealed, capped and closed as such is commonly carried out for intravenous solution, irrigation containers, and other package/containers as is commonly carried out by the prior art methods. Any of these well known manufacturing methods may be applied to carry out the intended scope of the present container/package invention as know by persons skilled in the art of practicing these manufacturing methods.

The enclosed drawings illustrate the invention using one of many such manufacturing processes, such as in a blow fill seal molding process. The utility of the invention may be carried out using any of the other aforementioned well know processes. The invention may also be carried out using manufacturing methods such as commonly done for intravenous solution containers, large volume and small volume parenteral solutions, and other types of irrigation solution containers by applying thermal, ultrasonic, and/or adhesive methods and/or combinations of the like, to sheets/strip of film, foil, or other suitable manufacturing material(s) thereby joining the layers of materials along what will form the periphery of an enclosure/barrier, the enclosure/barrier being formed and suitable for a non-leak seal and acting as a barrier sufficient to suitably protect the material(s)/content(s) on the inside from the outside exposure, and vice versa, until utilized in a course or treatment/care, and/or ultimate disposal.

It is understood that the inventions utility, methods, and apparatus may be carried out using a number of different manufacturing processes that are commonly know to those skilled in the art of making and manufacturing products in these field(s) such that the utility of reducing the numbers of products, containers, inventory, handling and other supply chain costs, as well as the utility of reducing medical waste may be carried out.

Sterilization

Devices used in the medical field are generally sterilized to a requirement as set forth for a particular purpose and applications. The materials and manufacturing methods employed must be suitable for the sterilization process of choice. These processes include Gamma radiation, electron beam, ETO, pulsed light etc. as some of the more common type of sterilization techniques. Some material(s)/content(s) are initially filled in a sterile environment as commonly practiced with blow fill seal technology. Any well known, well established manufacturing process is a viable candidate for the present invention provided such controls are in place to achieve the desired sterility assurance levels that are indicated for any particular indication. The intended scope of the invention is not dependent upon which method of sterilization is selected, in combination with at what point in time the material contents and the container/package becomes suitably sterile for use. Rather the intended scope of the contained/package invention's method and apparatus disclosed in this application is intended to cover the invention in all of the forms for which it may be made, manufactured, distributed, irregardless of its method of manufacture, material selection or method of achieving an indicated sterility assurance level (SAL) employed in preparation for its use and utility in the manufacture, distribution, use, re-use, collection and disposal of material(s)/content(s) thereby reducing the number of containers, reducing the costs, and reducing distribution and inventory and reducing other supply chain costs, such as a reduction in Activity Based Costing provided by the advent, object(s) methods and apparatus of the present container/package system(s) invention.

Industrial, Consumer, Commercial and Manufacturing Embodiments

It is understood the purpose of the herein disclosed invention and all of its applications and embodiments are not intended solely to the medical field and or not intended only for materials for treating and caring for humans and animals.

Volumetric displacement and volumetric replacement of dissimilar materials and volumetric displacement and volumetric replacement of materials of dissimilar origin, with respect to the prime manifold enclosure will be found to have a plurality of applications, combinations and sub-combination of uses and applications.

The inventor envisions many industrial, consumer, commercial and manufacturing applications. The following list of applications is not intended to limit to applications of the scope of the appended Claims. Additional field's of use outside of the medical field include the food industry, the chemical industry, the gas and fuel industry, the lubricant industry the beverage industry, automotive industry, aircraft industry, marine industry, solvent industry, paint industry, robotics industry, acids industry, adapter industry, aerospace, agriculture and air conditioner industries, the pharmaceutical industry, autoclave industry, soap and detergent industry, barrel industry, domestic and commercial products industry, blood industry, boat industry, military products industry, ammunition and weapons industry, bottle industry, can industry, box industry, cafeteria industry, bathroom supply industry, car industry, cement industry, ceramic industry, cleaning industry, machining industry, compound industry, containment and container industry, coolant industry, and the like. One need only finish reading the Index of the Thomas Register of Products and Services published annually by Thomas Publishing Company to identify further fields of use for the invention of volumetric displacement and volumetric replacement of dissimilar materials, and volumetric displacement and volumetric replacement of materials of dissimilar origin.

The inventor claims all of the forms of the present invention in all combinations and sub-combinations directed towards in the specification, and the drawing of the present case.

What is claimed is:

1. An efficient material(s)/content(s) container supply chain method comprising,
   receiving a prime manifold barrier said barrier manufactured to be adapted to enclose and commercialize fluid materials for displacing administration transfer said barrier having at least one port to be adapted for communication with an egressing conduit and positioned upstream to a first end configuration terminus in communication flow with a receiving source of a bodily delivery destination,
   removing said barrier from said egressing conduit said barrier being adapted to be positioned downstream in flow confining connection with an ingressing conduit said ingressing conduit communicating fluent material flow while interposed between said barrier and a second end form configuration terminus in flow communication with a dissimilar source of a bodily origin.

2. A method of claim 1 wherein said source of a bodily delivery destination comprises one bodily system and said dissimilar source of a bodily origin comprises a separate bodily system.

3. A method of claim 2 wherein said bodily delivery destination comprises a natural circulatory system and said bodily origin system comprises a natural alimentary canal system.

4. A method of claim 3 wherein a fluid enclosing barrier is in position upstream to egress fluid materials in flow control connection with said circulatory system and said barrier is in flow control connection downstream in position to ingress fluent materials in flow control connection with said alimentary canal system.

5. A method of claim 1 wherein said egressing conduit and said ingressing conduit are adaptable to be interposed between said barrier and said upstream position and said barrier and said downstream position with respect to said receiving source of a bodily delivery destination and said dissimilar source of a bodily origin.

6. A method of claim 1 wherein said egressing conduits terminate in said first end form configuration downstream to said barrier and in flow receptive communication with a blood vessel and said ingressing conduit terminates in said second end form configuration upstream to said barrier and in flow receptive communication with a natural alimentary canal system.

7. A method of claim 1 wherein said receiving source of a bodily delivery destinations comprises separate human and/or mammal anatomic locations.

8. A method of claim 2 wherein said dissimilar source of a bodily origins comprises separate human and/or mammal anatomic locations.

9. A method of claim 3 wherein said bodily delivery destinations and said bodily origins comprises separate human and/or mammal anatomic sources.

10. An environmentally preferred fluent material container supply chain and disposal chain method comprising,
    receiving a prime manifold barrier said barrier manufactured to contain and commercialize aseptic fluid materials said barrier having at least one port, said barrier being adapted to be in an upstream position for fluid material egress to a delivery destination,
    coapting said barrier with a fluid ingressing conduit said ingressing conduit interposed between said port and an end form configuration in flow control connection downstream in relation to an egressing source of material of a natural bodily origin.

11. A method of claim 10 wherein said delivery destination comprises one bodily system source and said egressing source of said material of a bodily origin comprises separate bodily system sources.

12. A method of claim 11 wherein said delivery destination comprises a natural circulatory system and said bodily origin comprises a natural alimentary canal system.

13. A method of claim 12 wherein the barrier is in position upstream to egress in flow control connection with said natural circulatory system and the barrier is in flow control connection downstream in position to ingress in flow control connection with said natural alimentary canal system.

14. A method of claim 12 wherein separate conduits being adapted to be interposed between said barrier and said delivery destination and said barrier and said bodily origins.

15. A method of claim 13 wherein egressing conduits terminate in a first end form configuration downstream to said barrier and in flow receptive communication with a blood vessel and said ingressing conduit terminates in a second end form configuration upstream to said barrier and in flow receptive communication with a natural alimentary canal system.

16. A method of claim 10 wherein said delivery destination comprises non natural sources.

17. A method of claim 10 wherein said egressing source of material of a bodily origin comprises separate human and/or mammal natural anatomic material emanating sources.

18. A method of claim 14 wherein said delivery destination and said bodily origins comprise separate sources being adaptable to control separate materials flow in association with said barrier at separate times.

19. An efficient and disposal chain fluent material containing supply chain method comprising,
    receiving a prime manifold barrier said barrier manufactured and commercialized containing fluid materials for said fluid displacement and administration transfer said barrier having at least one port being adapted to be coupled with an egressing conduit said barrier being positioned upstream to a first end form configuration terminus in communication with a flow receptive source of a bodily delivery destination,
    uncoupling said barrier from said egressing conduit said barrier being adapted to be connected to an ingressing conduit and positioned downstream to an origin of fluent material(s) of a bodily and other sources said barrier being in flow control communication with said ingressing conduit said ingressing conduit interposed between said origin of said fluent material(s) and said other sources and said barrier and pulling vacuum forces through said barrier said vacuum forces drawing said fluent material(s) downstream along said ingressing conduit toward and/or into said barrier.

20. A method of claim 19 wherein said sources of a bodily delivery destination comprise one bodily system and said origin of fluent materials of a bodily and other sources comprise emanating materials from separate sources.

21. A method of claim 20 wherein said bodily delivery destination comprises a natural circulatory system and said separate sources include a natural alimentary canal system and other said materials from said separate sources.

22. A method of claim 21 wherein said barrier is in position upstream to egress first materials in flow control connection with said natural circulatory system and said barrier is in flow control connection downstream in position to ingress second materials in flow control connection with said natural alimentary canal system.

23. A method of claim 19 wherein said egressing conduits being adapted to be interposed between said barrier and said first end configuration terminus and positioned upstream with respect to said delivery destination and said ingressing conduit being adapted to be interposed between said barrier and said second end form configuration positioned downstream with respect to said origin of fluent materials of a bodily and said other sources.

24. A method of claim 19 wherein said egressing conduits terminate in a first end form configuration downstream to said barrier and in flow receptive communication with a blood vessel and said ingressing conduit terminates in a second end form configuration upstream to said barrier and in flow receptive communication with a natural alimentary canal system.

25. A method of claim 19 wherein said bodily delivery destinations comprises separate human and/or mammal anatomic locations.

26. A method of claim 20 wherein said origin of fluent material(s) of a bodily and other sources comprises natural and/or non-natural materials sources.

27. A method of claim 21 wherein said bodily delivery destinations and said separate sources comprise separate human and/or mammal anatomic locations.

28. A fluent material container handling supply and disposal chain method comprising,
   receiving a prime manifold barrier said barrier manufactured to be adapted to contain and supply fluid material said barrier having at least one port said barrier being adapted to be in an upstream position for said fluid material egress to a delivery destination,
   adapting said barrier to be positioned in a downstream position relative to sources of natural and other origins of fluent material(s) said barrier being adapted to be in flow control communication with an ingressing conduit said ingressing conduit interposed between at least one of said ports and said sources and pulling vacuum forces through the barrier said vacuum forces drawing fluent material downstream from said sources towards and/or into said barrier.

29. A method of claim 28 wherein said delivery destination comprises non natural destination sources and said origin comprises separate sources of natural and other origins of fluent material.

30. A method of claim 28 wherein said delivery destination comprises a natural circulatory system and said origin comprises a natural alimentary canal system.

31. A method of claim 30 wherein a prime manifold barrier encloses fluid materials said barrier being adapted to be in position upstream to egress in flow control connection with said natural circulatory system and said barrier being adapted to be in flow control connection downstream in position to ingress fluent materials in flow control connection with said natural alimentary canal system.

32. A method of claim 31 wherein an egressing conduit being adapted to be interposed between said barrier and said destination and in flow association with said barrier while in said upstream position and an ingressing conduit being adapted to be interposed between said barrier and said origin and in flow association with said barrier while in said downstream position said barrier being adaptable for efficient upstream supply and downstream disposal of dissimilar material(s) of dissimilar origin and intended for dissimilar delivery destinations.

33. A method of claim 30 wherein said egressing conduits terminate in a first end form configuration downstream to said barrier and in a first flow receptive communication with a natural blood vessel and said ingressing conduit terminates in a second end form configuration upstream to said barrier and in a second flow receptive communication with a natural alimentary canal system.

34. A method of claim 28 wherein said delivery destinations comprise separate sources.

35. A method of claim 29 wherein said origins comprise separate sources.

36. A method of claim 28 wherein wherein said destinations comprises an open top sterile receptacle.

37. A supply and disposal chain method of containing fluent materials comprising,
   receiving a prime manifold barrier said barrier manufactured to be adapted to contain and commercialize fluid materials said barrier having at least one port said barrier being adapted to be in an upstream position for said fluid materials egress into an open receptacle,
   adapting said barrier downstream to an ingressing conduit said conduit being composite said composite conduit being adapted to be interposed between a natural bodily system and a source of suction said source of suction being adaptable to draw fluent materials downstream along said composite conduit for fluent materials flow towards and/or for said fluent materials ingress into said barrier.

38. A method of claim 37 wherein said delivery destination comprises an open top receptacle adapted to be in a sterile condition for receiving said fluid materials and said natural bodily system comprises a natural airway.

39. A method of claim 37 wherein said composite conduit is adapted to be in position to ingress fluent materials towards and/or into said barrier said composite conduit adapted to be interposed between said source of suction draw said natural airway said barrier adapted to be interposed between said conduit and said source of suction.

40. A method of claim 39 wherein said ingressing composite conduit is adapted to be interposed between said source of suction draw and said natural airway said draw being adapted to draw fluent materials along said ingressing composite conduit for clearing said airway, said ingressing composite conduit adapted for coupling at one end with a suction wand, said ingressing conduit adapted for coupling at the other end to said barrier and said source of suction.

41. A method of claim 37 wherein said bodily system comprises a natural respiratory system.

42. A method of claim 37 wherein said fluid material egress being interposed between said barrier and said delivery destination said barrier being adapted to be in a position downstream relative to said natural airway said fluent flow being interposed between said bodily system and said barrier for said flow along said conduit towards and/or for fluent materials ingressing into said barrier.

43. A method of claim 40 wherein said fluent materials are drawn away from said airway by said vacuum force along said ingressing conduit.

44. A method of claim 38 wherein said fluent materials are drawn toward and/or into said barrier from proximal to distal along said composite conduit said fluent materials drawn toward and/or into said barrier from along a distal opening in said alimentary canal.

45. A method of claim 37 wherein fluent materials are drawn from a natural alimentary canal system.

46. A method of claim 28 wherein fluent materials are drawn from a natural alimentary canal system.

47. A method of claim 1 wherein said barrier is provided for containment and conditioning and disposing said fluent materials.

48. A method of claim 10 wherein said barrier is provided for containment and conditioning and disposing said materials.

49. A method of claim 19 wherein said barrier is provided for containment and conditioning and disposing said materials.

50. A method of claim 28 wherein said barrier is provided for containment and conditioning and disposing said materials.

51. A method of claim 37 wherein said barrier is provided for containment and conditioning and disposing said fluent materials.

52. A method of claim 45 wherein said fluent materials are drawn toward and/or into said barrier from distal to proximal along said composite conduit said fluent materials drawn toward and/or into said barrier from along a proximal opening in said alimentary canal.

* * * * *

UNITED STATES PATENT AND TRADEMARK OFFICE
CERTIFICATE OF CORRECTION

PATENT NO. : 7,798,181 B2  
APPLICATION NO. : 11/638867  
DATED : September 21, 2010  
INVENTOR(S) : Jack W Romano It is certified that error appears in the above-identified patent and that said Letters Patent is hereby corrected as shown below:

Column 1, line 30: delete "bu" and substitute --by-- in its place.
Column 1, line 55: delete "die" and substitute --the-- in its place.
Column 2, line 53: delete "defines" and substitute --define-- in its place.
Column 3, line 59: delete "reaches" and substitute --teaches-- in its place.
Column 5, line 42: delete the second "the" and delete "or" and substitute a third --of-- in its place to read "distinct disciplines of each of the prior art.".
Column 8, line 18: delete ", incoming fluent" ending the sentence with the --.--.
Column 9, line 44: delete "configtrations" and substitute --configurations-- in its place.
Column 10, line 36: delete "recover" and substitute --recovery-- in its place.
Column 11, line 18: delete "sea" and substitute --seal-- in its place.
Column 11, line 22: delete "enclosure" and substitute --enclose-- in its place.
Column 11, line 58: delete "harrier" and substitute --barrier-- in its place.
Column 12, line 10: delete "patil(s)" and substitute --path(s)-- in its place.
Column 14, line 5: insert --at-- between "that" and "junction" to read "that at junction" and delete "ill".
Column 14, line 56: delete "housing".
Column 16, line 47: delete "container" and substitute --containers-- in its place.
Column 21, line 51: delete "die" and substitute --the-- in its place.
Column 21, line 52: insert --,-- between "Rather" and "the". Delete "just".
Column 26, line 6: delete "inured" and substitute --injured-- in its place.
Column 26, line 27: delete "diletantes" and substitute --dilutants-- in its place.
Column 28, line 27: delete "example" and substutite --examples-- in its place.
Column 29, line 43: delete "t" and substitute --the-- in its place.
Column 33, line 28: delete "ma)" and substitute --may-- in its place.
Column 33, line 53: delete "suitable" and substitute --suitably-- in its place.
Column 34, line 11: delete "know" and substitute --known-- in its place.
Column 34, line 36: delete "contained" and substitute --container-- in its place.
Column 36, line 55 (Claim 19): delete "and" and insert --and-- substituting its position in the sentence between "chain" and "fluent" to read "An efficient disposal chain and fluent material......".

Signed and Sealed this

Thirtieth Day of November, 2010

David J. Kappos  
*Director of the United States Patent and Trademark Office*